United States Patent
Consigny et al.

(10) Patent No.: US 9,687,239 B2
(45) Date of Patent: Jun. 27, 2017

(54) INTRAVASCULAR DEVICES SUPPORTING AN ARTERIOVENOUS FISTULA

(71) Applicant: Abbott Cardiovascular Systems Inc., Santa Clara, CA (US)

(72) Inventors: Paul Consigny, San Jose, CA (US);
Erik Eli, Redwood City, CA (US);
Stephen D. Pacetti, San Jose, CA (US);
Mikael Trollsas, San Jose, CA (US);
John Stankus, Campbell, CA (US);
Julia Fox, San Carlos, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 245 days.

(21) Appl. No.: 14/253,719

(22) Filed: Apr. 15, 2014

(65) Prior Publication Data
US 2015/0289875 A1    Oct. 15, 2015

(51) Int. Cl.
*A61F 2/06* (2013.01)
*A61B 17/11* (2006.01)
(Continued)

(52) U.S. Cl.
CPC ............... *A61B 17/11* (2013.01); *A61F 2/856* (2013.01); *A61F 2/89* (2013.01); *A61F 2/91* (2013.01);
(Continued)

(58) Field of Classification Search
CPC .. A61F 2/82; A61F 2/852; A61F 2/856; A61F 2/95; A61F 2/954; A61F 2/962;
(Continued)

(56) References Cited

U.S. PATENT DOCUMENTS

| 6,022,359 A | 2/2000 | Frantzen |
| 6,245,104 B1 | 6/2001 | Alt |

(Continued)

FOREIGN PATENT DOCUMENTS

| WO | WO 01/39699 A1 | 6/2001 |
| WO | WO 2009/129481 A1 | 10/2009 |

(Continued)

OTHER PUBLICATIONS

Paddle. (n.d.). Dictionary.com Unabridged. Retrieved Mar. 30, 2016 from Dictionary.com website http://www.dictionary.com/browse/paddle.*

(Continued)

*Primary Examiner* — Jonathan Miles
*Assistant Examiner* — Kankindi Rwego
(74) *Attorney, Agent, or Firm* — Squire Patton Boggs (US) LLP

(57) ABSTRACT

Medical devices and methods for forming an arteriovenous (AV) fistula include a stent having an arterial tubular portion and vein supporting tongue connected by a pre-shaped connector and a venous frustoconical stent having a distal end for maintaining a take-off angle for the venous portion of the AV fistula. Also disclosed is an angled balloon for assisting with the formation of the AV fistula. The medical devices disclosed herein support an AV fistula formation having a desired take off angle of about 30 degrees, or between about 15 and 45 degrees.

14 Claims, 17 Drawing Sheets

(51) Int. Cl.

| | | |
|---|---|---|
| *A61F 2/91* | (2013.01) | |
| *A61F 2/954* | (2013.01) | |
| *A61F 2/856* | (2013.01) | |
| *A61F 2/89* | (2013.01) | |
| A61F 2/958 | (2013.01) | |
| A61M 1/36 | (2006.01) | |
| A61F 2/848 | (2013.01) | |
| A61F 2/966 | (2013.01) | |
| A61F 2/82 | (2013.01) | |
| A61F 2/915 | (2013.01) | |

(52) U.S. Cl.
CPC ....... *A61F 2/954* (2013.01); *A61B 2017/1107* (2013.01); *A61B 2017/1135* (2013.01); *A61F 2/064* (2013.01); *A61F 2/848* (2013.01); *A61F 2/958* (2013.01); *A61F 2/966* (2013.01); *A61F 2002/821* (2013.01); *A61F 2002/828* (2013.01); *A61F 2002/91575* (2013.01); *A61F 2002/9583* (2013.01); *A61M 1/3655* (2013.01)

(58) Field of Classification Search
CPC ...... A61F 2/966; A61F 2/97; A61F 2002/821; A61F 2002/823; A61F 2002/825; A61F 2002/826; A61F 2002/828; A61F 2002/9505; A61F 2002/9511; A61F 2002/9665; A61F 2/064; A61F 2/086; A61F 2002/065; A61F 2002/067; A61F 2002/068; A61B 17/11; A61B 2017/1103; A61B 2017/1107; A61B 2017/111; A61B 2017/1121; A61B 2017/1135
See application file for complete search history.

(56) References Cited

U.S. PATENT DOCUMENTS

| | | | |
|---|---|---|---|
| 6,641,605 B1 | 11/2003 | Stergiopulos | |
| 6,663,664 B1 | 12/2003 | Pacetti | |
| 6,858,035 B2 | 2/2005 | Whayne | |
| 7,625,400 B2 | 12/2009 | Bowe et al. | |
| 7,758,634 B2 * | 7/2010 | Brucker | A61F 2/856 623/1.35 |
| 8,236,040 B2 * | 8/2012 | Mayberry | A61F 2/07 623/1.11 |
| 2003/0009183 A1 | 1/2003 | Whayne | |
| 2003/0125802 A1 | 7/2003 | Callol et al. | |
| 2004/0146546 A1 | 7/2004 | Gravett et al. | |
| 2006/0155239 A1 | 7/2006 | Knudson et al. | |
| 2006/0173534 A1 | 8/2006 | Das | |
| 2006/0184232 A1 | 8/2006 | Gianotti et al. | |
| 2007/0142897 A1 | 6/2007 | Consigny et al. | |
| 2008/0027533 A1 * | 1/2008 | Oepen | A61F 2/856 623/1.35 |
| 2008/0082046 A1 | 4/2008 | Kato et al. | |
| 2008/0091263 A1 | 4/2008 | Iyer et al. | |
| 2008/0319367 A1 | 12/2008 | Crawley et al. | |
| 2009/0234431 A1 | 9/2009 | Weinberger et al. | |
| 2010/0114290 A1 | 5/2010 | Rasmussen et al. | |
| 2010/0244304 A1 | 9/2010 | Wang | |
| 2010/0298952 A1 | 11/2010 | Busold et al. | |
| 2011/0066222 A1 | 3/2011 | Wang et al. | |
| 2011/0319976 A1 | 12/2011 | Iyer et al. | |
| 2012/0065652 A1 | 3/2012 | Cully et al. | |
| 2012/0073733 A1 | 3/2012 | Ngo et al. | |
| 2012/0330437 A1 | 12/2012 | El-Kurdi et al. | |
| 2013/0041453 A1 | 2/2013 | Consigny | |
| 2013/0085563 A1 | 4/2013 | Stankus et al. | |
| 2013/0110153 A1 * | 5/2013 | Wang | A61F 2/013 606/200 |
| 2013/0338762 A1 | 12/2013 | Jayasinghe et al. | |
| 2014/0046431 A1 | 2/2014 | Hossainy et al. | |

FOREIGN PATENT DOCUMENTS

| | | |
|---|---|---|
| WO | WO 2013192208 A1 * | 12/2013 |
| WO | WO 2014/020565 A1 | 2/2014 |
| WO | WO 2014020565 A1 * | 2/2014 |

OTHER PUBLICATIONS

Deswal A, Tamang BK, Bala A. Study of Aortic-Common Iliac Bifurcation and Its Clinical Significance. Journal of Clinical and Diagnostic Research:JCDR 2014;8(7):AC06-AC08. doi.7860/JDCR/2014/8767.4559.*
Span. American Heritage dictionary, Retrieved Dec. 26, 2016 http://www.thefreedictionary.com/span.*
International Search Report and Written Opinion of the International Searching Authority mailed on Oct. 8, 2015, for related PCT application No. PCT/US2015/026007, 19 pp.
U.S. Appl. No. 14/063,984, filed Oct. 25, 2013, Consigny et al.
Asif et al. "Early Arteriovenous Fistula Failure: A Logical Proposal for When and How to Intervene", Am. Soc. of Nephrology, pp. 332-339 (2006).
Anastomosis, Medline Plus Medical Encyclopedia, 1 pg. (2012).
Bettinger et al., "Three-Dimensional Microfluidic Tissue-Engineering Scaffolds Using a Flexible Biodegradable Polymer", Adv. Mater. 18, pp. 165-169 (2006).
Carlier et al., "Augmentation of Wall Shear Stress Inhibits Neointimal Hyperplasia After Stent Implantation: Inhibition Through Reduction of Inflammation?", Circulation, Jour. Am. Heart Assoc. vol. 107, pp. 2741-2746 (2003).
El-Kurdi et al., "Transient Elastic Support for Vein Grafts Using a Constricting Microfibrillar Polymer Wrap", Biomaterials, 29, pp. 3213-3220 (2008).
Ene-Iordache et al., "Effect of anastomosis angle on the localization of disturbed flow in 'side-to-end' fistulae for haemodialysis access", Nephrol Dial Transplant 28, pp. 997-1005 (2013).
Fistula, Medline Plus Medical Encyclopedia, 1 pg. (2011).
Guan et al., "Preparation and Characterization of Highly Porous, Biodegradable Polyurethane Scaffolds for Soft Tissue Applications", Biomaterials 26, pp. 3961-3971 (2005).
Krishnamoorthy et al., "Anatomic configuration affects the flow rate and diameter of porcine arteriovenous fistulae", Kidney International 81, pp. 745-750 (2012).
Murphy "Reducing In-Stent Restenosis Through Novel Stent Flow Field Augmentation", Cardiovascular Eng. and Tech., vol. 3, No. 4, pp. 353-373 (2012).
Papachristou et al., "From basic anatomic configuration to maturation success", Kidney International 81, pp. 724-726 (2012).
Paulson et al., "Safety and efficacy of local periadventitial delivery of sirolimus for improving hemodialysis graft patency: first human experience with a serolimus-eluting collagen membrane (Coll-R)", Nephrol Dial Transplant vol. 27, pp. 1219-1224 (2012).
Roy-Chaudhury et al. "Hemodialysis Vascular Access Dysfunction—Opportunities for Targeting an Unmet Clinical Need", Touch Briefings, pp. 1-4 (2007).
Roy-Chaudhury et al., "Novel Therapies for Hemodialysis Vascular Access Dysfunction: Fact or Fiction!", Blood Purif., vol. 23, pp. 29-35 (2005).
Roy-Chaudhury et al., "Vascular Access in Hemodialysis: Issues, Management, and Emerging Concepts", Cardio Clinics vol. 28, pp. 249-273 (2005).
Zangan et al., "Optimizing Arteriovenous Fistula Maturation", Seminars in Interventional Radiology vol. 26, No. 2, pp. 144-150 (2009).

* cited by examiner

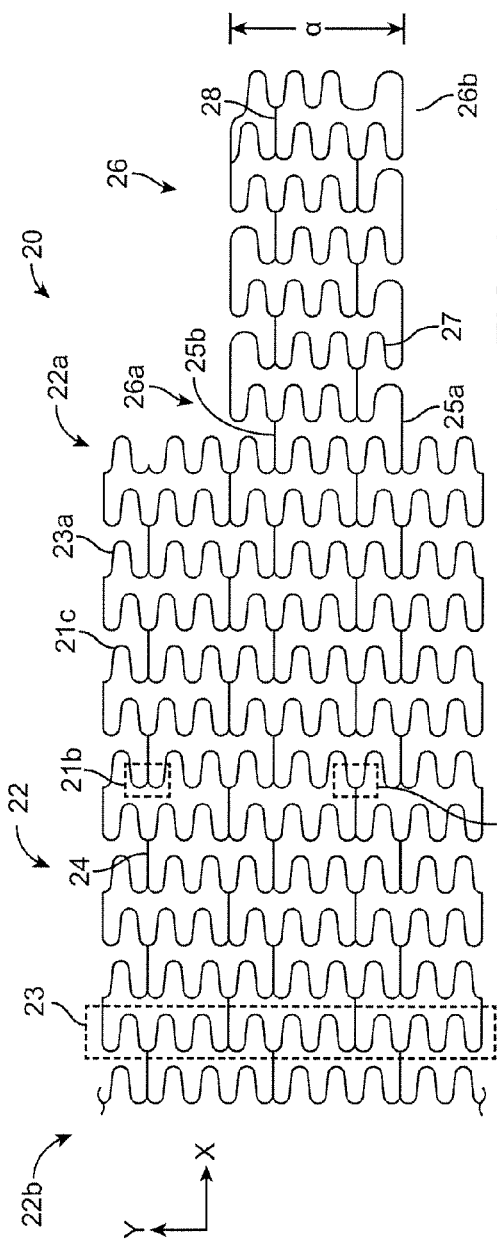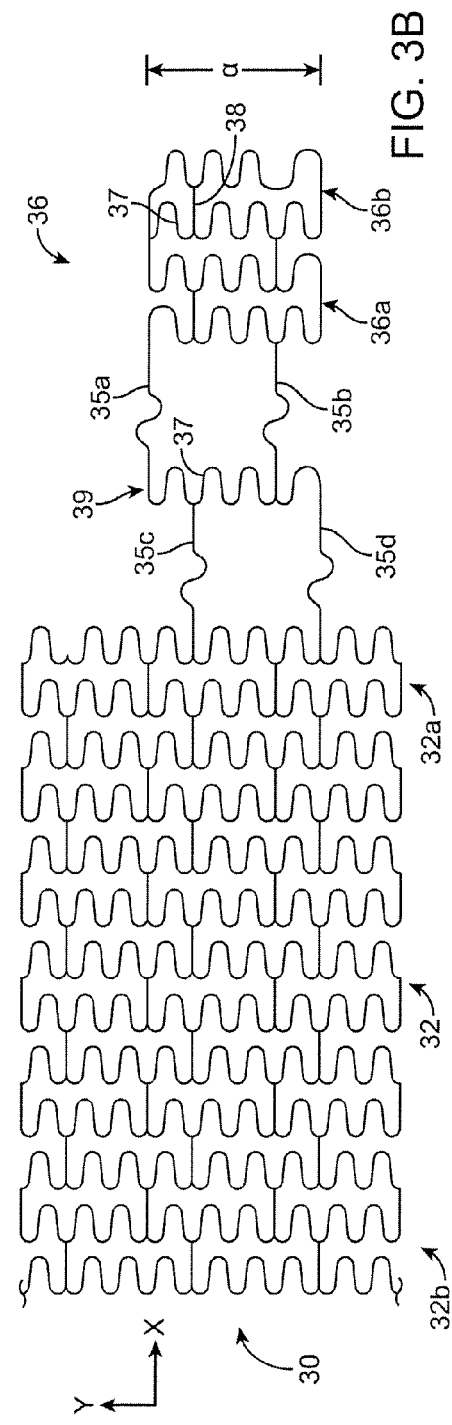

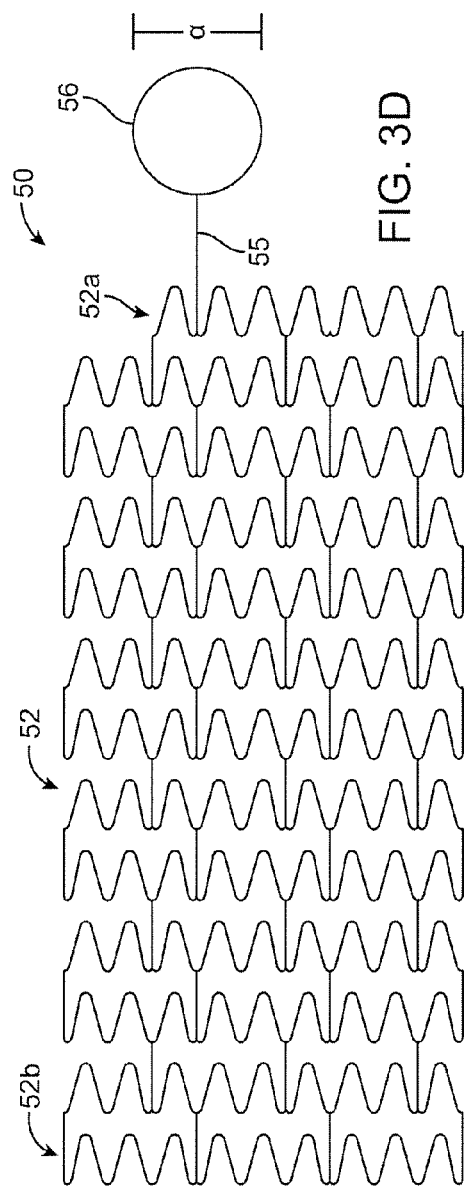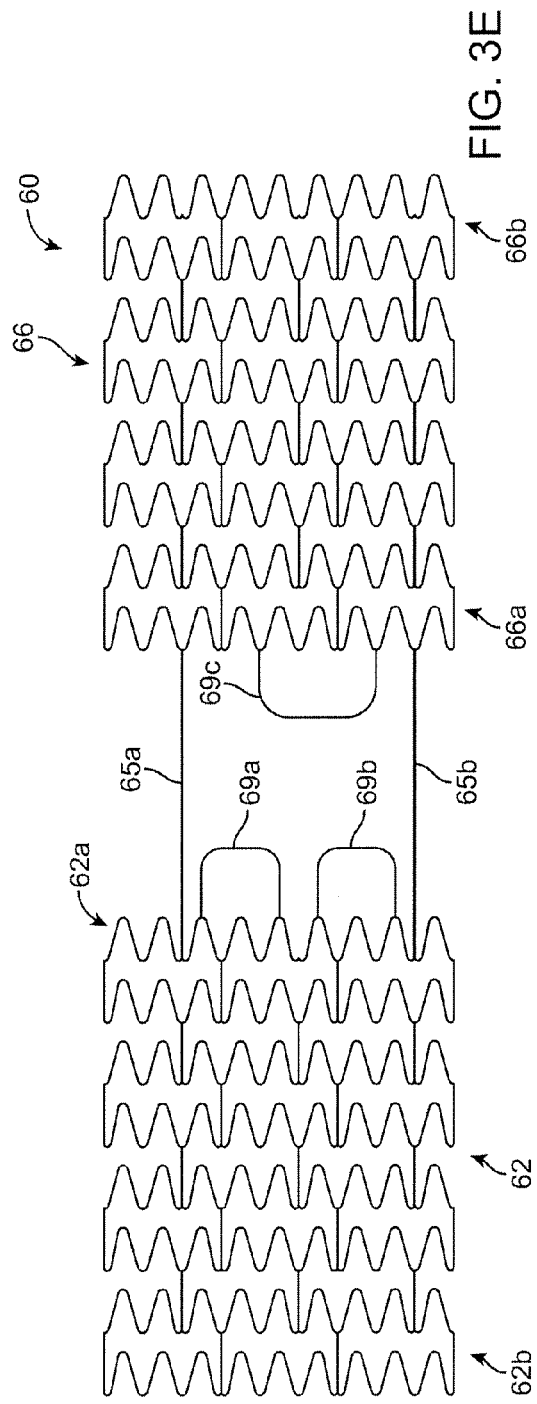

INTRAVASCULAR DEVICES SUPPORTING AN ARTERIOVENOUS FISTULA

FIELD OF THE INVENTION

The present invention relates to implantable medical devices associated with the creation of, and/or the maturation of an arteriovenous (AV) fistula access structure for hemodialysis.

BACKGROUND OF THE INVENTION

AV Fistula (a connection between an artery and a vein) are a desired access structure for the dialysis of kidney failure patients. FIG. 12 illustrates a matured portion of the vein near the artery, which acts as a re-usable cannula access site proximal the AV fistula.

About 42% of surgically created AV Fistula fail to mature; that is, the portion of the vein proximal the fistula fails to adapt physiologically to accommodate the higher arterial pressure. When this venous portion (or side of the AV fistula) matures, it becomes usable as a cannula access site for dialysis (FIG. 12). Maturation can take about 6 weeks from surgically forming the fistula. Failure to mature and/or act as a good dialysis access site is most commonly the result of poor blood flow (low blood pressure/low blood flow rates) in the venous portion of the fistula. About 74% of these failures are salvaged by some form of intervention, followed by maturation of the venous side in another 6-8 weeks. The remaining about 11% of the cases are regarded as failures, which necessitates creating an AV Fistula at another site. The most common site of initial AV Fistula creation is the fore arm. If a new AV Fistula is required, a new site proximal of the previous/failed site is chosen. Typically, there are 3 potential sites per arm.

Patients without a mature AV Fistula require some other, less desirable form of dialysis access for the standard 3 times a week dialysis regimen until a mature fistula is available. Additionally, about a third of mature fistula fail in a year. The health of kidney failure patients without a functioning mature AV Fistula deteriorates at a more rapid rate than those with one. Deteriorating health makes the subsequent creation of a functioning mature AV Fistula less probable, necessitating a significant number of interventions or access procedures resulting in poorer survival rates. Thus, a significant number of interventions and procedures may be avoided or significantly delayed, significant cost savings realized and the survival rate of dialysis patients significantly improved by decreasing the failure to mature rate of newly created AV fistula and by reducing the rate at which mature fistula fail.

There is evidence that the shape of an arteriovenous fistula can affect long term durability. For example, Papachristou (2012) and Krishnamoorthy (2012) have indicated that a curved fistula is preferred to a straight fistula because the curved fistula results in greater flow rates, lesser differences in wall shear stress, greater venous dilatation, and less eccentric neointimal hyperplasia. Papachristou E and Vazquez-Padron R I. *From basic anatomic configuration to maturation success*. Kidney International 81: 724-726, 2012. Krishnamoorthy M K, Banerjee R K, Wang Y et al. *Anatomic configuration affects the flow rate and diameter of porcine arteriovenous fistula*. Kidney International 81: 745-750, 2012. In addition, Ene-lordache B et al (2013) have found that angle at the origin of a "side-to-end" arteriovenous fistula is very important. Their research indicates that an angle of 30 degrees is preferred over angles of 45, 60 or 90 degrees. Ene-lordache B, Cattaneo L, Dubini G, Remuzzi A. *Effect of anastomosis angle on the localization of disturbed flow in "side-to-end" fistula for haemodialysis access*. Nephrol Dial Transplant 28: 997-1005, 2013.

There are no known intraluminal devices available that can effectively and reliably assist a surgeon in creating a more desirable AV fistula construct, to maintain the desired geometry after surgery, and/or to support maturation and extended patency of the fistula. Accordingly, there is a need for an intraluminal device that can aid in creating the correct anatomy by providing the appropriate support in the appropriate locations and in the appropriate configurations that promote long-term arteriovenous (AV) fistula patency.

SUMMARY OF THE INVENTION

The invention provides an intraluminal apparatus and method for forming, supporting and/or assisting with the formation of an AV fistula. The apparatus is intended for being placed at an anastomosis to support and help achieve a vein maturation including an about 15 to 45 degrees, preferably about 30 degree, take-off angle (or less than about 45 degrees) between the vein and artery at the fistula. In some embodiments the apparatus is placed prior to forming the anastomosis and provides assistance with attaching the vein to the artery in the desired manner. In some embodiments the apparatus remains at the anastomosis after the surgery and helps produce proper vein maturation including the about 30 take-off angle. In some embodiments the apparatus both helps with attaching the vein to the artery and achieving maturation by remaining implanted after the fistula is formed.

U.S. application Ser. No. 14/063,984 disclose extravascular wraps for an AV fistula. Discussed therein are take-off angles for the venous portion of the fistula and related problems. The application is considered as part of this disclosure and is fully incorporated herein.

The invention, in one aspect, is directed to a medical device supporting a desired venous take off angle of about 30, or between about 15-45 degrees. This angle helps decrease failure to mature rates. Take-off angles above about 45 degrees (relative to the artery longitudinal axis), has been associated with low flow of the fistula. Loss of (or poor) patency of the attachment site is associated with low flow and eventual failure of the fistula.

Reducing the rate at which mature fistula fail is accomplished by providing an implanted device, referred to herein as an AV stent or scaffold. According to the disclosure, a stent or scaffold has the following attributes:
  installed at the time of surgery to make the AV fistula;
  a tubular body is implanted in the arterial portion of the fistula immediately upstream and/or downstream of the fistula, or in the venous portion of the fistula;
  a flange, tongue or petals attached to the tubular body extends from the tubular body to the venous or arterial portion of the fistula, respectively, to support the fistula and promote formation of the desired take-off angle as the vein matures; and
  the stent and scaffold help increase blood flow by reducing blood flow turbulence near the fistula and/or increasing wall shear stress.

According to another aspect of the disclosure there is a balloon formed to make an angle between a proximal and distal portion thereof equal to the desired take-off angle for the fistula. The balloon is placed and inflated prior to joining the vein to the artery. The balloon's presence assists the surgeon with setting the vein in place and supporting the vein at the take-off angle as it is being connected to the artery.

According to one aspect of the disclosure, a primary purpose of the tongue is to set the angle θ between the artery and the vein. Angle α determines how much of the vein circumference is covered or directly supported by the tongue when implanted. An angle of 360 degrees means the tongue is a tube, which the vein must fit around. However, the tongue also has a radius in the Z-Y plane. This radius would ideally match that of the vein. After the fistula is formed, the vein enlarges with successful maturation of the fistula. During this change, however, the tongue may potentially become malapposed with respect to the vein if it is made as a complete cylinder, i.e., a diameter of essentially fixed size. Hence, by having the tongue span an angle of less than 360 degrees, e.g. 180 degrees or even less than 180 degrees, the tongue's presence, with its accompanying neointimal formation, is more likely to be in full apposition with the vein wall. Another aspect is the goal of minimizing the amount of stent or scaffold in the vein. While the tongue serves as a guide, all stents have associated risks of thrombosis and restenosis which are only exacerbated by increasing the amount of stent in the vein. This is another motivation for minimizing the length and circumference of the tongue only to what is needed for it to function as a guide.

A lengthwise extent, i.e., extent measured along the X-axis for the tubular and tongue portions when mounted on the catheter, is selected according to a new for establishing and sufficiently providing support to the fistula so that the angle Θ can be maintained during the time period of about 6 weeks from formation of the fistula. As will be appreciated selection of those lengths or relative lengths for the tubular portion and tongue should moreover be balanced against the need to avoid adverse effects, e.g., low shear stress, oscillatory flow, etc., due to the presence of the implanted stents. Thus, a length or more desirably a ratio of lengths, which can then be suitably sized for different anatomy, balances the need for avoiding, e.g., a stenosis developing, and what is necessary to provide stability and guidance for the vein. The ratio of tongue length to tubular portion length may range from 1/3 to 3/1. For the tubular portion the ratio of length to the deployed diameter may range from 1.5/1 to 4/1.

In accordance with the foregoing, there is an AV stent or scaffold, medical device, method for making such an AV stent or scaffold, a method of using an AV stent or scaffold, or method for assembly of a medical device comprising such a AV stent or scaffold, and/or a medical device comprising a balloon, having one or more, or any combination of the following things (1)-(49):

(1) A stent or scaffold. 4
(2) A medical device including a stent mounted on a catheter.
(3) A tubular body configured for being implanted in a venous or arterial portion of an AV fistula.
(4) A beveled edge, flange, and/or petals configured to form with the tubular body a take-off angle Θ of about 30, or between about 15-45 degrees.
(5) A tongue which that extends from the artery into the vein. The tongue is connected to the tubular portion by one, two, three, four or a plurality of connecting elements.
(6) Lengths for a tubular and tongue portion to provide stability and guidance for the vein. The ratio of tongue length to tubular portion length may range from 1/3 to 3/1. For the tubular portion the ratio of length to a deployed diameter may range from 1.5/1 to 4/1.
(7) The connector is pre-set to deflect away from the longitudinal axis of the tubular body when unrestrained, so that the tongue forms the take-off angle Θ.
(8) The plurality of connecting elements include a central connector element configured for being placed at the carina of the fistula; and/or elements having an S-shape. The S-shaped elements have a bending stiffness less than the central connector.
(9) The tongue spans an arc length angle α, which is about 270, 180, or 90 degrees, of about 90-180 degrees.
(10) A taper for a frustum or tongue is 1:2, 1:3, 1:1.5 or between about 1:1.5 (i.e., a frustum diameter distal of the fistula is 1.5 times greater than a diameter proximal the fistula) to 1:3 (i.e., a frustum diameter distal of the fistula is 3 times greater than the diameter proximal the fistula).
(11) The connectors can be offset from each other by α/2 or α/4.
(12) A cylindrical or frusto-conical body having a radially expandable structure characterized by a pattern including rings connected by links.
(13) The pattern is a repeating pattern of Y-W-U crowns. There may be one, two or three U crowns between each Y and W crown. Or there may be no U crowns between a Y and W crown.
(14) A tubular portion having a paddle connected through a connector.
(15) A stent according to any of FIGS. 3A-3D, as a self-expanding or balloon expandable stent.
(16) A stent having a first tubular portion and second tubular portion interconnected by two connectors. The stent has a plurality of petals extending between the tubular portions.
(17) A petal having a flexible wire filling the space within a petal, or the petal is a sheet of material to limit prolapse.
(18) A catheter including the stent and a sheath disposed over the stent.
(19) A curved distal portion of the catheter. A distal tip of the catheter may turn through an angle of between about 60 to 90 degrees; and/or a restraining sheath restraining a stent, or a crimped stent or scaffold may turn through an angle of between about 60 degrees, or about 60 to 90 degrees.
(20) The sheath including a first sheath and a second sheath, or one sheath disposed over the stent.
(21) The catheter including a pusher rod and tether for removing a first sheath and second sheath from the stent, respectively.
(22) The catheter including rims, edges, flanges or islands for retaining the stent on the catheter.
(23) The catheter including a balloon.
(24) The stent, tubular portion and/or frustum are cut from a tube and are radially expandable by a balloon or self-expanding.
(25) A self-expanding stent or a balloon expandable stent mounted to the catheter.
(26) A frustum or frusto-conical stent including a bevel at an end configured for being located proximally to the fistula.
(27) A self-expanding device forming a frustum wherein the frustum shape is pre-set, e.g., if nitinol the frustum is a heat set shape.
(28) A balloon expanded device crimped to a balloon that when deployed takes on a frustoconical shape. The frustoconical stent is configured to form a larger diameter at one end furthest the fistula and smaller diameter at the opposite end.

(29) The frustum having a bevel that has the shape of a half-sinusoid.

(30) The frustum having petals extending about the bevel and configured to maintain the take-off angle.

(31) A frustum constrained to expand by biodegrading or bioresorbable filaments.

(32) A plurality of petals disposed about the beveled edge of the frustum and configured to deflect away from the stent longitudinal axis and become flush with the artery wall.

(33) A venous stent that is drug eluting, where the drug can be everolimus, sirolimus and paclitaxel.

(34) A balloon catheter having an angled balloon. The balloon has one or two lobes. When one lobe the lobe is configured for being placed upstream of an arterial opening. When two lobes a first lobe is placed downstream, and the other lobe is placed upstream of the arterial opening.

(35) A balloon configured to form the take-off angle Θ at the arterial opening of a fistula.

(36) A balloon having a distal portion, waist and a proximal portion. The distal portion, waist and proximal balloon portions have inflated diameters Da, Dg and Dv respectively. Da>Dv>Dg. The waist position is disposed between the distal portion and proximal portion.

(37) A surgical guide for forming a fistula.

(38) One or two guidewires pre-shaped to form the take-off angle Θ

(39) A method for making a fistula according to FIG. 1A-1F, 6A-6H, 7A-7F, 8A-8J, or 10A-10C.

(40) An intraluminal medical device, comprising a stent or scaffold, including a tubular portion, a tongue, and a connector connecting the tongue to the tubular portion; wherein the connector is pre-shaped to cause the tongue to form an angle (Θ) of about 30 or between about 15 to 45 degrees with respect to a bore axis of the tubular portion.

(41) The aspects of disclosure as set forth in (40) in combination with one of, more than one of, or any combination of the following list of things: wherein the tubular portion is a radially expandable body having a plurality of rings interconnected by struts; wherein the tongue spans an angle of less than 360 degrees; wherein the connector comprises a plurality of link elements; wherein the tongue is tapered; wherein the connector includes a first plurality of links interconnected by a second plurality of links through a transitional structure; wherein the tongue is a paddle; wherein the paddle is a wire and includes a second wire extending across a space surrounded by the paddle; and/or wherein the connector includes a central, straight connector and two S-shaped connectors surrounding the straight connector; wherein the stent or scaffold, respectively, may be made from a super elastic material, a metal or alloy, a biodegradable metal, a biodegradable and/or shape memory polymer or a bioresorbable polymer.

(42) A catheter comprising a medical device retained within a sheath at the distal end of the catheter; wherein a first sheath constrains a tubular portion and a second sheath constrains a tongue; and/or the tubular portion and tongue are retained between a proximal ledge and a distal ledge.

(43) A method of forming a fistula using the medical device of (40), (45), (46) or (48).

(44) A method of forming an arteriovenous (AV) fistula, comprising the steps of: providing a stent having a first portion and a second portion; placing the first portion in an arterial portion of the AV fistula and the second portion outside of the arterial portion, wherein the second portion is orientated at an angle (Θ) of about 30 or between about 15 to 45 degrees with respect to a bore axis of the first portion.

(45) An intraluminal medical device, comprising: a frustum, a beveled distal edge of the frustum, and a member attached to the distal edge and pre-shaped to form an angle (Θ) of about 30 or between about 15 to 45 degrees with respect to a bore axis of the frustum. The member may take the form of a plurality of pre-shaped petals configured to deflect away from the bore axis of the frustum.

(46) A catheter comprising the medical device of (45), wherein the frustum is wrapped within a plurality of filaments configured to restrain the frustum to take the shape of a cylinder having a proximal end diameter equal to about a distal end diameter.

(47) The medical device of (45) or (46) in combination with one of, more than one of, or any combination of the following list of things: wherein the frustum comprises a radially expandable body cut from a tube and forming interconnected elements including a plurality of rings connected by links; the frustum is a balloon expandable body crimped to a balloon configured to expand to a frustoconical shape; the expandable body is formed with a plurality of rings connected by links, where bar arms or struts of the ring increase in length from a proximal to distal end, and/or the number of crests increase in proportion to the taper of the frustum.

(48) An apparatus, comprising a balloon catheter, the balloon including a distal portion having an inflated diameter Da, a proximal portion having an inflated diameter Dv, and a waist portion having an inflated diameter Dg, wherein when the balloon is in an inflated state the distal portion is arranged at an angle (Θ) of about 30 or between about 15 to 45 degrees with respect to a longitudinal axis of the catheter.

(49) The apparatus of (48) in combination with one of, more than one of, or any combination of the following list of things: wherein the balloon includes a downstream balloon portion and upstream balloon portion; wherein the balloon includes a downstream balloon portion and upstream balloon portion; and/or wherein the downstream portion forms an angle of (180−Θ) and the upstream portion forms the angle Θ.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 3A shows a flattened 2D representation of a first alternative embodiment of the stent or scaffold depicted in FIGS. 2A-2B.

FIG. 3B shows a flattened 2D representation of a second alternative embodiment of the stent or scaffold depicted in FIGS. 2A-2B.

FIG. 3D shows a flattened 2D representation of a fourth alternative embodiment of the stent or scaffold depicted in FIGS. 2A-2B.

FIG. 3E shows a flattened 2D representation of a fifth alternative embodiment of the stent or scaffold depicted in FIGS. 2A-2B. According to this embodiment the tongue is replaced by petals and the tubular portion includes an upstream and downstream tubular portion configured for being implanted in the arterial portion of the fistula.

DETAILED DESCRIPTION OF EMBODIMENTS

Figure 1A:
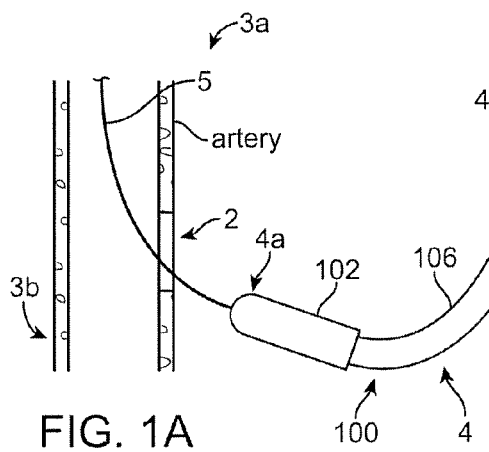
FIGS. 1A through 1F depict steps associated with a procedure for forming an arteriovenous (AV) fistula according to a first aspect of the disclosure. The procedure includes the use of a catheter having a stent or scaffold. The stent or scaffold has a tubular portion, tongue portion and connector connecting the tongue to the tubular portion. The stent or scaffold is used to support the formation of the AV fistula so that the venous portion of the fistula forms with the arterial portion a desired take-off angle Θ. The tubular portion of the stent or scaffold is placed upstream of the fistula.

For purposes of this disclosure, the following terms and definitions apply:

When referring to a vein or artery prior to making a fistula, a "proximal end" refers to an end closest to the torso of the body, whereas a "distal end" refers to the end furthest from the torso of the body. In contrast, after the fistula is made, or when referring to a medical device's intended location relative to a fistula or anastomosis, the terms "proximal" and "distal" are instead intended to be made with respect to the relative location of the fistula or anastomosis. Thus, for example, the end of a scaffold closest to the fistula will be called the "proximal" end and the end furthest from the fistula the "distal" end. Thus, generally speaking, prior to making the fistula the former terminology is used. And after the fistula is made "proximal" and "distal" always refers to a location relative to the fistula.

The terms "anastomosis" and "fistula" may be used interchangeably in this description. For purposes of the disclosure the two terms mean the same thing and refer to the arteriovenous (AV) type of anastomosis or fistula.

A "tongue" as used herein refers to a long and narrow projection that serves as a guide or support for assembly, and/or as a securing device when an AV fistula is made. A tongue is supported from an end of a tubular body as a cantilever. Additionally, a tongue is connected to an end of a tubular body by a link having shape memory where the link is configured to orient the tongue at the take-off angle Θ with respect to a bore axis of the tubular body.

A "petal" is a U-shaped, arched or curvilinear element that extends from a crown or valley of a ring or undulating member of a scaffold or stent structure to a different crown or valley of the same ring or undulating member. An example is petal 69c shown in FIG. 3E, which extends between and is connected to different U-crowns of the same ring.

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, or between 1-2%, 1-3%, 1-5%, or 0.5%-5% different from d2. If d1 is a mean value, then d2 is about d1 means d2 is within a one-sigma, two-sigma, or three-sigma variance from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

A "stent" is a permanent structure, usually comprised of a metal or metal alloy, generally speaking, while a "scaffold" is a structure comprising (at least in-part) a biodegradable or bioresorbable polymer, biodegradable metal or alloy, or combination thereof capable of radially supporting a vessel for a limited period of time, e.g., 3, 4, 6 or 12 months following implantation. It is understood, however, that the art sometimes uses the term "stent" when referring to either type of structure.

A "crimping" or "inelastic crimping" of a stent or scaffold to a balloon means, unless otherwise stated, a significant plastic or inelastic deformation of the stent or scaffold (body), such that when a radial restraint is removed from the crimped body, e.g., a constraining sheath is withdrawn, the scaffold or stent will change diameter (due to elastic recoil) by no more than about 5%, 10%, 20%, 30% or 50% increase from the crimped diameter. A body crimped to the balloon is held to the balloon by a retention force. A crimped body is deployed within the body by a balloon that imposes a significant inelastic or plastic deformation to expand the body to a deployed, expanded or post-dilation diameter. The crimped body when deployed also has elastic recoil causing it to reduce in diameter by no more than about 1, 2, 1-5%, 5-10% or 10%.

Figure 2A:
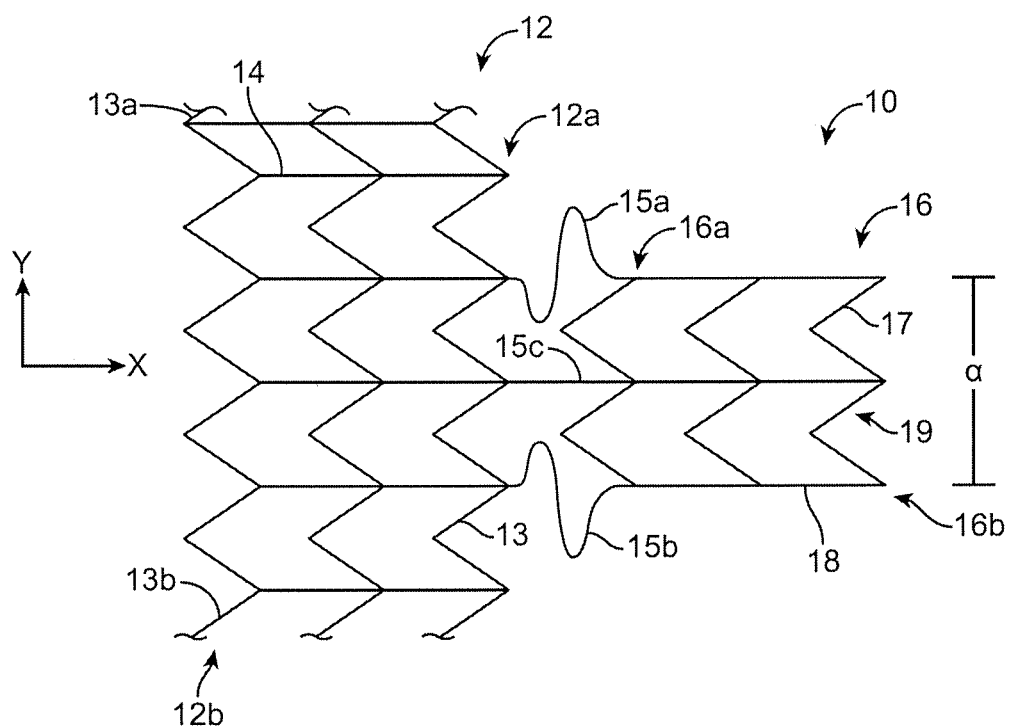
FIGS. 2A and 2B show a 2D flattened view and deployed or expanded side view, respectively, of the stent or scaffold used in the steps of FIGS. 1A through 1F.
Figure 2B:
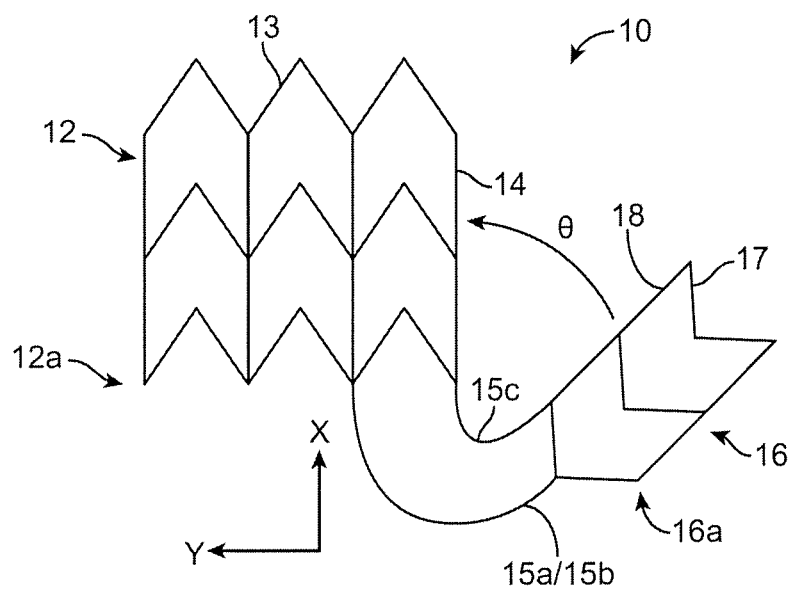

A procedure for forming an AV fistula is explained in the '984 application, in connection with FIGS. 2A-2C of the '984 application. As noted therein, after the fistula is formed, there is no guarantee that the vein will retain a desirable flow facilitating curve. An AV stent or scaffold according to the disclosure helps to maintain a desired venous shape to increase the patency period for the fistula. Importantly, the devices disclosed herein can promote increased flow rate through the fistula by affecting the flow characteristics/patterns such that there are no regions of low wall shear stress and/or less circular/stagnant flow along in the vein wall, which helps prevent a stenosis from forming at the fistula or adjacent portions of the vein. Preferably the AV stent or scaffold (or combination thereof) is such that it causes the vein to mature into a shape producing a relatively low acceleration (rate of direction change) of the flow as it is diverted from the artery to vein. Moreover, the shape minimizes or eliminates stagnant or circular blood flow and avoids the forming of low flow regions that result in minimal or no shear stress along the vessel walls. Dimensional goals for the fistula are to enlarge to a diameter on the order of 6 mm and lie no more than 6 mm beneath the skin surface.

Referring to FIGS. 1A-1F, 2A, 2B, and 3A-3E, there is shown aspects of an AV stent or scaffold according to a first disclosure. FIGS. 1A-1F illustrates the creation of the AV fistula using the AV stent or scaffold of FIGS. 2A-2B. FIGS. 3A-3E illustrate different embodiments of the AV stent or scaffold or FIGS. 2A-2B. In the following discussion, reference is mostly made with respect to stent embodiments; however, the same description also applies to scaffold embodiments.

Figure 1D:
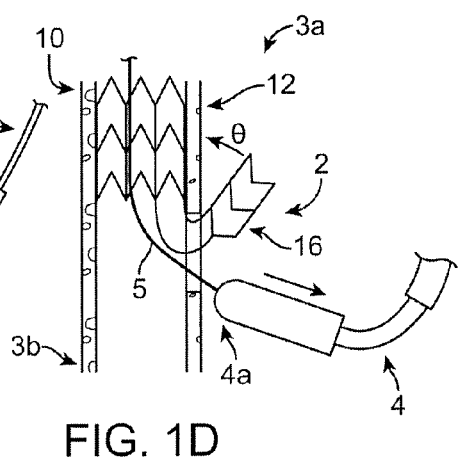
Figure 1B:
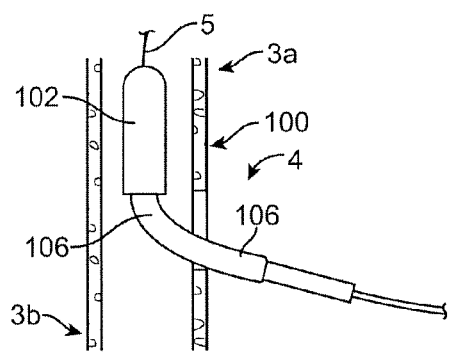

Referring to FIG. 1A, after an opening 2 is made in the artery between an upstream or proximal end 3a and distal or downstream end 3b, a guide wire 5 is passed through the opening 2 and extended towards the upstream end 3a. The guidewire 5 is a curved guide wire to facilitate placement of the prosthesis in the desired location and setting of the desired take off angle at the fistula without imposing undue stress on the blood vessel. A catheter 4 having a distal end 4a is passed over the guide wire 5 and placed at a location immediately upstream of the opening 2, as shown in FIG. 1B.

The catheter 4 has at its distal end 4a a medical device 100 including an AV stent 10 encased within sheaths 102 and 106. FIG. 1C shows the stent 10 after the sheaths 102, 106 are removed. The stent 10 includes a tubular portion 12 and tongue portion 16, which assume deployed or expanded forms as shown in FIG. 1C after the sheaths 102, 106 are removed (FIG. 1C shows sheath 106 within the bore of the tubular body expanded in the artery. When deployed the sheath 106 is pushed upstream more towards location 3a shown in FIG. 1C, then pulled back through the deployed body 12 towards the catheter proximal end). The tongue 16 forms an angle $\Theta$ with the tubular portion 12 and extends outwardly from the opening 2. Referring to FIG. 1D, after the stent 10 is placed the catheter 4 is withdrawn from the opening 2, followed by the guide wire 5.

Figure 1E:
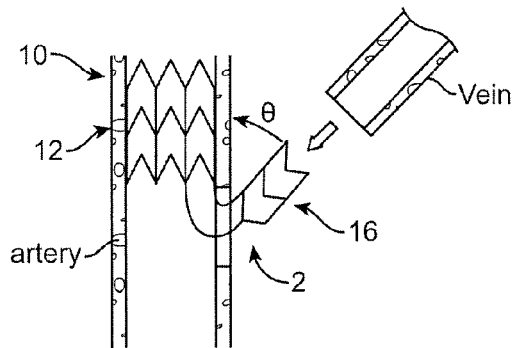
Figure 1C:
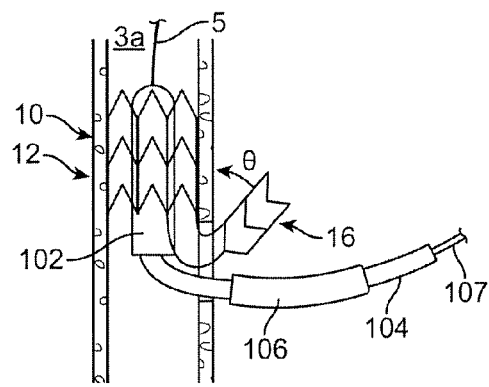
Figure 1F:
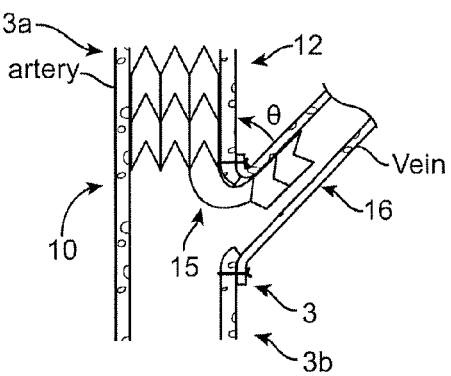

Referring to FIGS. 1E and 1F, with the stent 10 deployed and in the desired orientation having the tongue 16 extend from the opening 2 and forming the take-off angle $\Theta$ with the tubular portion 12, the vein is attached, e.g., by suturing 3. After attachment the tubular portion 10 and tongue 16 remain at the fistula to assist with maturation of the vein including maintaining the take-off angle $\Theta$ as the vein matures. The tongue 16 may be sutured to the vein to help hold the vein in place.

Figure 3C:
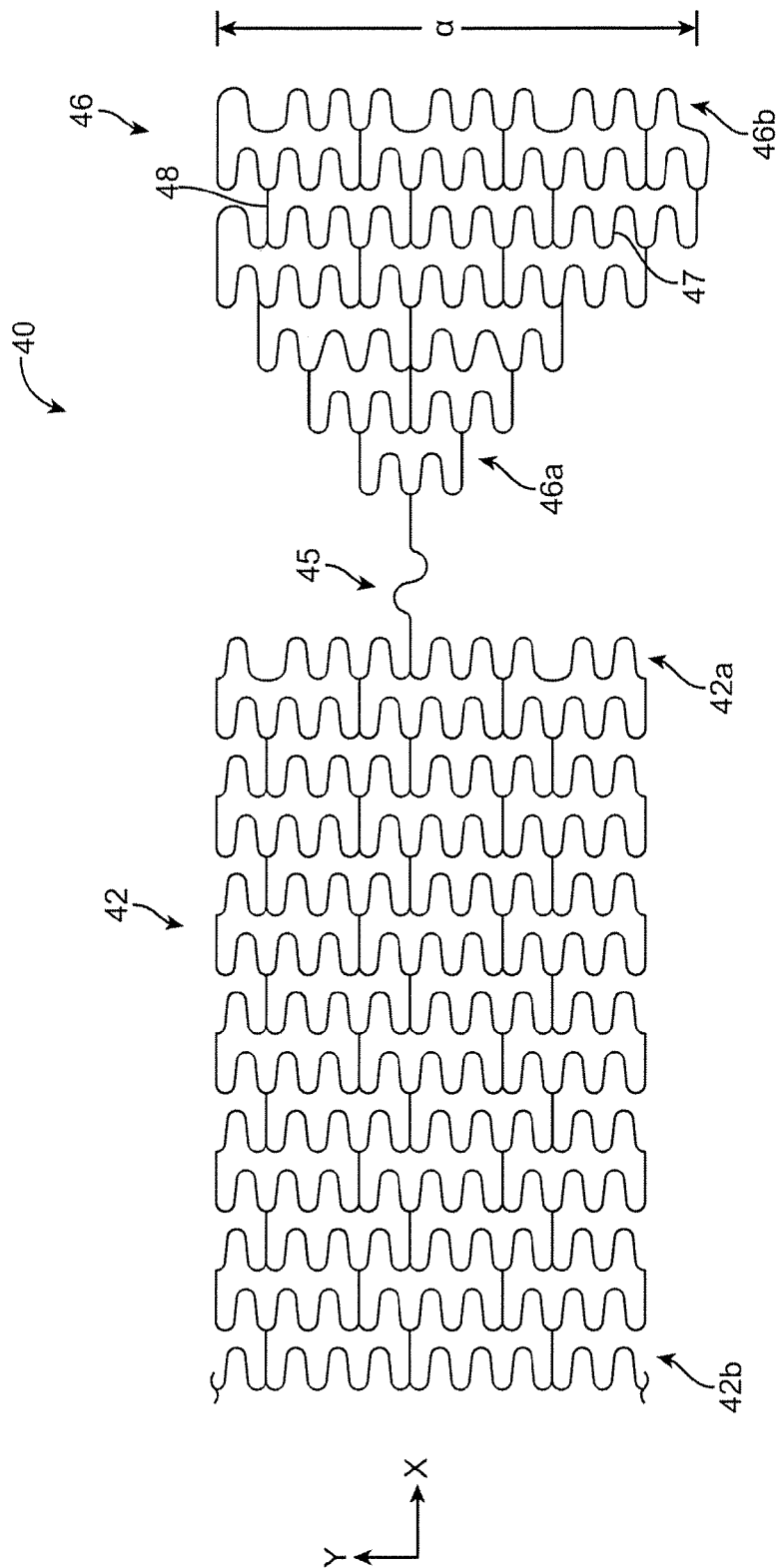
FIG. 3C shows a flattened 2D representation of a third alternative embodiment of the stent or scaffold depicted in FIGS. 2A-2B.
Figure 4A:
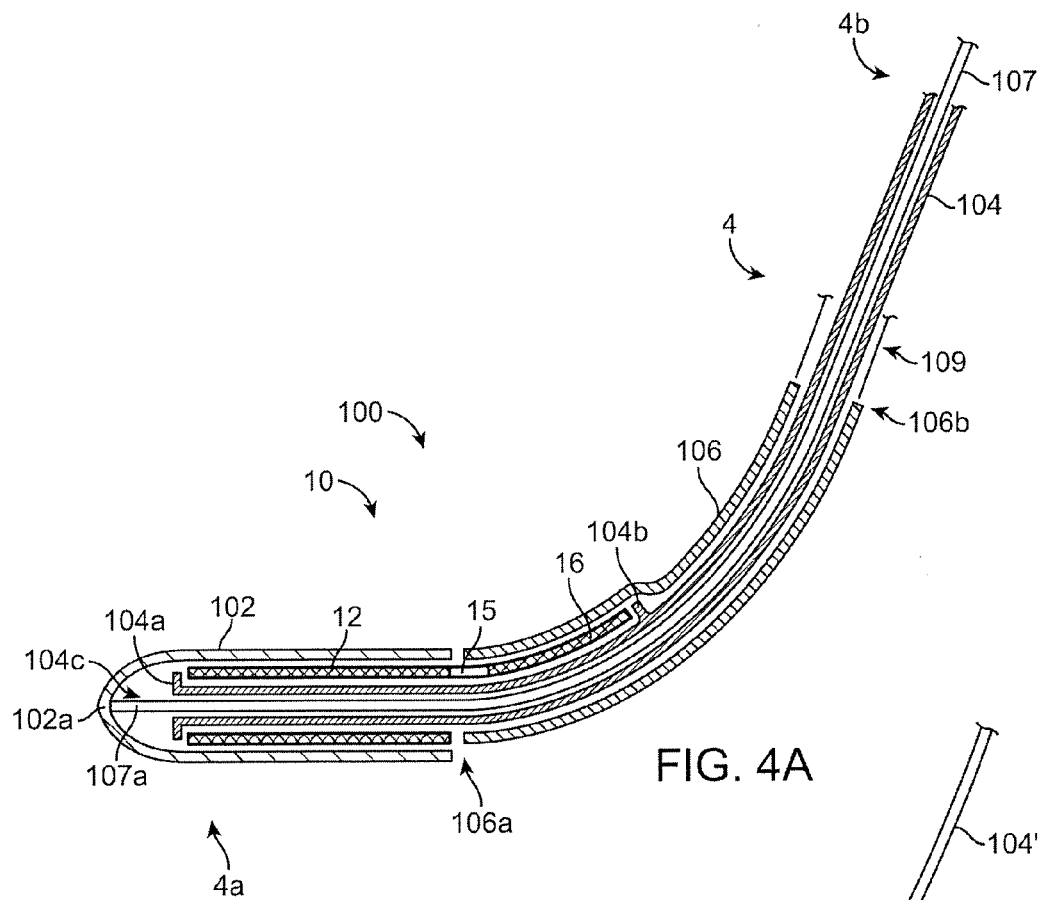
FIG. 4A is a side-cross sectional view of a distal portion of the catheter used to deliver the stent or scaffold of FIGS. 2A-2B according to the steps of FIGS. 1A-1F. According to this embodiment the stent or scaffold is self-expanding.

FIG. 2A shows a planar view of the stent 10 when encased within the sheaths 102, 106 (FIG. 4A shows a cross-sectional view of the stent 10 when encased within the sheaths 102, 106). FIG. 2B shows a side view of the same stent 10 when deployed at the fistula (FIG. 1F). Referring to FIG. 2A, the tubular portion 12 includes a plurality of ring elements 13 (three in this example) interconnected by link elements 14. The tubular portion 12 resembles a cylinder when deployed or removed from the sheath 102 (the ends 13a, 13b indicate the same strut portion of the ring 13, which are connected). The tubular portion 12 has a bore or longitudinal axis parallel to the X-axis shown and a transverse axis (perpendicular to the longitudinal axis) that is parallel to the Y axis (This convention of showing the cut-open planar view of the tubular body 12, longitudinal and transverse axes, and coordinates X-Y in FIG. 2A is adopted for the stent embodiments shown in FIGS. 3A-3E). The tubular portion 12 furthermore has a proximal portion 12a (proximal meaning nearest the fistula, FIG. 1F) and a distal portion 12b (distal meaning furthest from the fistula.

The tongue 16 includes several plurality of interconnected struts 17 each forming an undulating pattern 19 extending over the angle $\alpha$ (three such undulating patterns shown in FIG. 2A). The angle $\alpha$ may be thought of corresponding to the circumferential portion of the vein that the tongue can directly support when implanted. Adjacent undulating patterns 19 are interconnected to each other by links 18 (six links shown in FIG. 2A). The tongue 16 spans the angle $\alpha$, which is less than 360 degrees about the X axis in FIG. 2A. The tongue 16 has curvature in the Y-Z plane that may be described as tracing the arc of a circle. In use, the angle of this circular arc is represented in the planar view by the angle $\alpha$, which can be about 270, 180, or 90 degrees, of about 90-180 degrees.

According to one aspect of the disclosure, a primary purpose of the tongue is to set the angle $\theta$ between the artery and the vein. Angle $\alpha$ determines how much of the vein circumference is covered or directly supported by the tongue when implanted. An angle of 360 degrees means the tongue is a tube, which the vein must fit around. However, the tongue also has a radius in the Z-Y plane. This radius would ideally match that of the vein. Just as with other medical devices, this endovascular device can be made with a matrix of sizes to accommodate both different artery and vein sizes. With regard to an AV fistula, the vein will enlarge with successful maturation of the fistula. During this change of the vein size, however, the tongue may potentially become malapposed with respect to the vein if it is made as a complete cylinder, i.e., a diameter of essentially fixed size. Hence, by having the tongue span an angle of less than 360 degrees, e.g. 180 degrees or even less than 180 degrees, the tongue's presence, with its accompanying neointimal formation, is more likely to be in full apposition with the vein wall. Another aspect is the goal of minimizing the amount of stent or scaffold in the vein. While the tongue serves as a guide, all stents have associated risks of thrombosis and restenosis which are only exacerbated by increasing the amount of stent in the vein. This is another motivation for minimizing the length and circumference of the tongue only to what is needed for it to function as a guide.

Consistent with, and as mentioned above, the angle α (alpha) having an angle of 180 degrees or less has the following advantages:

As stent will induce intimal thickening, this limits the amount of lumen loss to less than or equal to one-half of circumference;

May limit endothelial injury/preserve more endothelium needed to prevent thrombosis and restenosis and promote remodeling;

Allows the area to be more flexible, deformable; and

Allows the vein to expand (remodel) with increased blood flow

The tongue 16 includes a proximal end 16a (nearest the fistula) and a distal end 16b (furthest form the fistula). The tongue 12 may be tapered from the proximal end to the distal end where the ratio of taper (i.e., change in size of the arc α) may be about 1:2, 1:3, 1:1.5 or between about 1:1.5 to 1:3, where the distal end 16b has the larger arc length than the proximal end 16a. This taper may be desirable as a means for accommodating or encouraging an increase in diameter of the venous portion of the fistula as the vein matures. Or the taper may be desired from a stress-strain standpoint. By having a tapered tongue stress concentrations near the connector 15 attachments can be reduced.

The tongue 16 may, in some embodiments, be considered as a continuation of the tubular portion 12 in the sense that the arc angle α measuring an arc length is measured with respect to the same reference as for the tubular portion 12 when the stent 10 is in the stowed state; that is, the center of the circle from which the angle α is measured lies on the longitudinal axis or the radius of curvature is the same as the center and radius of curvature, respectively, associated with the cylindrical body 12. Indeed, in some embodiments the tongue 16 may be formed or cut form the same tube as the tubular portion 12. The tongue 16, however, does not circumscribe the longitudinal axis whereas the tubular portion 12 does circumscribe the axis X. The tongue 16 maximum extent is indicated by arc angle α.

The tongue 16 is connected to the tubular portion 12 by flexible connectors 15. In FIG. 2A there are three connectors 15a, 15b, and 15c connecting the tongue 16 to the tubular portion 12. In the embodiment depicted in FIGS. 2A-2B there is a central connector 15c and side connectors 15a, 15b on opposite sides of the central connector 15c. The side connectors 15a, 15b are formed to have S-shaped or generally more flexible properties, and the ability to accommodate more elongation, as compared to the central connector (i.e., the combined flexural rigidity of the connectors 15a, 15b measured in the X-Y bending plane of FIG. 2B is less than the flexural rigidity of the central connector 15c. According to some embodiments the combined flexural rigidity of the connectors 15a, 15b measured in the X-Y bending plane of FIG. 2B is about 1/2 the flexural rigidity of the central connector 15c to accommodate an increased range of motion when the tongue 12 is configured from the stowed state (FIGS. 2A, 4A) to the deployed state shown in FIG. 2B. Comparing FIGS. 2A, 2B and 4A, when the tongue 16 is moved from its stowed state (FIGS. 2A and 4A) to its deployed state (FIG. 2B) the connectors 15a, 15b are deformed or re-shaped more than the connector 15c, as can also be appreciated from the greater distance between the ends 16a and 12a for the connectors 15a, 15b than connector 15c in the deployed state (FIG. 2B).

As can be appreciated from FIGS. 1E and 1F the connectors 15 are relied on for maintaining the angle Θ and supporting the vein when it is attached and/or serving as a guide for the surgeon placing the vein in position when the fistula is being formed. The center connector 15c is placed at the carina of the fistula.

In some embodiments the stent 10 can be made entirely from a super elastic alloy, such as nitinol, elgiloy, or strain hardened stainless steel, e.g., as disclosed in U.S. Pat. No. 6,663,664 to Pacetti (with or without the variable radial force feature using a biodegradable polymer). The stent 10 could also be made from a self-expanding biodegradable metal or polymeric material.

In the case of nitinol, the stent 10 could first be manufactured by laser cutting the desired pattern from a nitinol tube. After the body is laser cut and polished, it would be placed into a fixture to set the expanded shape for the target diameter artery (portion 12) and take-off angle Θ relative to the portion 12 (heat set of the connectors 15). With nitinol, this placement into a fixture is referred to as heat setting. In general, a temperature as low as 400 degrees C. and durations of 1-2 minutes can set the shape, but often temperature used are closer to 500 degrees C. with times over 5 minutes. After heat setting, the device will take the form of stent 10 in FIG. 2B. The stent 10 may be compressed to its stowed form in FIG. 4A and self-expands to the shape shown in FIG. 2B when the restraining sheaths 102, 106 are removed.

According to the disclosure, the lengthwise extent, i.e., extent measured along the X-axis for the tubular and tongue portions when mounted on the catheter, is selected according to a new for establishing and sufficiently providing support to the fistula so that the angle Θ can be maintained during the time period of about 6 weeks from formation of the fistula. As will be appreciated selection of those lengths or relative lengths for the tubular portion and tongue should moreover be balanced against the need to avoid adverse effects on blood flow, e.g., low shear stress, oscillatory flow, etc., due to the presence of the implanted stents. Thus, a length or more desirably a ratio of lengths, which can then be suitably sized for different anatomy, balances the need for avoiding, e.g., a stenosis developing, and what is necessary to provide stability and guidance for the vein. The ratio of tongue length to tubular portion length may range from 1/3 to 3/1. For the tubular portion the ratio of length to the deployed diameter may range from 1.5/1 to 4/1.

FIGS. 3A through 3E depict alternative embodiments of the stent 10 described in connection with FIGS. 1A-1F and 2A-2B. In the following description where the same element numbering as used previously is used again, the same description will apply. FIG. 3A depicts a stent 20 having a tubular portion 22 and a tongue 26 connected to each other by a connector 25. The discussion given previously in connection with the stent 10 applies to stent 20, except as noted below.

The tubular portion 22 has a plurality of undulating ring elements 23 interconnected by links 24. A total of 13 ring elements 23 are shown (for example). The ring 23 type and connectivity between the rings 23 and links 24 may be described as follows. The tubular portion 22 is a nine crown and three link 24 pattern, meaning each ring 23 has nine crowns (either a W-crown, Y-crown, or U-crown) and three links connect the ring 23 to an adjacent ring. A "Y-crown" refers to a crown 21*a* where the angle extending between a strut 23*a* and a link 24 at the crown 21*a* is an obtuse angle (greater than 90 degrees). A "W-crown" refers to a crown 21*b* where the angle extending between the strut 23*a* and the link 24 is an acute angle (less than 90 degrees). A U-crown is a crown 21*c* not connected to a link 24. The connectivity pattern between adjacent rings 23 is a repeating pattern of Y-crown, W-crown, U-Crown, or Y-W-U-Y-W-U-Y-W-U (etc.). And the tubular portion 22 has at most three links connecting rings.

The tongue 26 has several of a plurality of interconnected struts 27 each forming an undulating pattern extending over the angle α and interconnected by links 28. At the proximal end 26*a* of the tongue 26 there are two connectors 25*a*, 25*b* which may be the same as other links 28 of the tongue 26. According to the embodiment of FIG. 3A the tongue portion 22 and tubular portion 26 may be cut from a tube and formed using the same repeating pattern of Y-W-U-Y-W-U. The only difference between the tubular body 22 and tongue 26 being that the tongue has the angle α, which is less than 360 degrees. Or the tongue has at most two links 28 between undulating struts 27 whereas the tubular portion 22 has at most three links 24 interconnecting rings 23.

In other embodiments the pattern of Y, W and U crowns may vary. For example, there may be two or three U crowns between a W or Y crowns and there may be no U crowns between a Y crown and a W crown. Moreover, there may be more than three links connecting rings. Or no links connecting rings. In the latter case rings may be coupled to each other, joined or attached by, e.g., spot welding rings together.

FIG. 3B depicts a stent 30 having a tubular portion 32 and a tongue 36 connected to each other by connectors 35. The discussion given previously in connection with the stent 10 applies to stent 30, except as noted below.

The discussion provided earlier in connection with the structure and pattern for tubular portion applies to the tubular portion 32. Thus, tubular portion 32 also has undulating rings interconnected by links and forming a repeating pattern of Y-crown, W-crown, U-Crown, or Y-W-U-Y-W-U-Y-W-U (etc.).

The tongue 36 has several of a plurality of interconnected struts 37 each forming an undulating pattern extending over the angle α and interconnected by links 38. The proximal end 36*a* is connected to a pair of S-shaped connectors 35*a*, 35*b*. The connectors 35*a*, 35*b* connect end 36*a* to a transitional structure 39 formed by undulating struts 37. The intermediate structure 39 is connected to the proximal end 32*a* of the tubular portion 32 by a second set of connectors 35*c*, 35*d* that may also be S-shaped. This transitional structure 35*a*, 35*b*, 35*c*, 35*c*, 35*d* and 39 of the connector portion of the stent 50 may be preferred for purposes of making it easier to, in the case of nitinol, heat set the angle α, reducing stress concentrations where connectors 35 connect to the tubular portion 32 and/or tongue 36 and maintaining the angle α when the tongue portion 36 is released from the sheath 106. The connectors 35 are offset from each other. For example, each of the connectors 35 may be spaced by at least α/4 or at most α/2 degrees offset from the nearest connector, or so that there is one or two U-crowns between any pair of connectors 35.

FIG. 3C depicts a stent 40 having a tubular portion 42 and a tongue 46 connected to each other by connector 45. The discussion given previously in connection with the stent 10 applies to stent 40, except as noted below.

The discussion provided earlier in connection with the structure and pattern for tubular portion 22 applies to the tubular portion 42. Thus, tubular portion 42 also has undulating rings interconnected by links and forming a repeating pattern of Y-crown, W-crown, U-Crown, or Y-W-U-Y-W-U-Y-W-U (etc.).

The tongue portion 46 has several of a plurality of interconnected struts 47 each forming an undulating pattern extending over the angle α and interconnected by links 48, as was the case for tongue portions 26 and 36. However, the tongue 46 illustrated in FIG. 3C is tapered along its length. The width or arc corresponding to α at the proximal end 46*a* is a smaller length than at the distal end 46*b*, as shown. The ratio of corresponding lengths or arc lengths for the distal end 46*b* to the proximal end 46*a* may be about 2:1, 3:1, 4:1 or between about 3:1 to 6:1. As indicated earlier, a tapered tongue 46 may be desired as a means for accommodating or encouraging an increase in diameter of the venous portion of the fistula as the vein matures. Additionally, the taper provides a transition from flexible (near connector) to more supportive. Or the taper may be desired from a stress-strain standpoint. By having a tapered tongue 46 stress concentrations near the connector 45 attachment can be reduced. There is only one connector 45 for this embodiment.

FIG. 3D depicts a stent 50 having a tubular portion 52 and a tongue 56 connected to each other by connector 55. The discussion given previously in connection with the stent 10 applies to stent 50, except as noted below.

The discussion provided earlier in connection with the structure and pattern for tubular portion 22 applies to the tubular portion 52. Thus, tubular portion 52 also has undulating rings interconnected by links and forming a repeating pattern of Y-crown, W-crown, U-Crown, or Y-W-U-Y-W-U-Y-W-U (etc.).

The tongue portion 56 for this embodiment is a paddle 56, which may be elliptical and made from a flat or curved sheet with its largest extent, e.g., diameter of a circle, along the Y-axis extending over the angle α. The paddle 56 may be circular, rectangular or more generally polygonal. There is a single straight connector 55 connecting the paddle 56 to a proximal end 52*a* of the tubular portion 52. The paddle may be a wire frame or solid, sheet of material which provides support. Preferably material occupies the area within a wire frame embodiment of 52 to limit prolapse.

FIG. 3E depicts a stent 60 having a downstream arterial portion 62 and an upstream arterial portion 66 connected to each other by connectors 65. The discussion provided earlier in connection with the structure and pattern for tubular portion 22 applies both to the portion 62 and portion 66 of the stent 60. Thus, portions 62 and 66 each have undulating rings interconnected by links and forming a repeating pattern of Y-crown, W-crown, U-Crown, or Y-W-U-Y-W-U-Y-W-U (etc.).

Figure 3F:
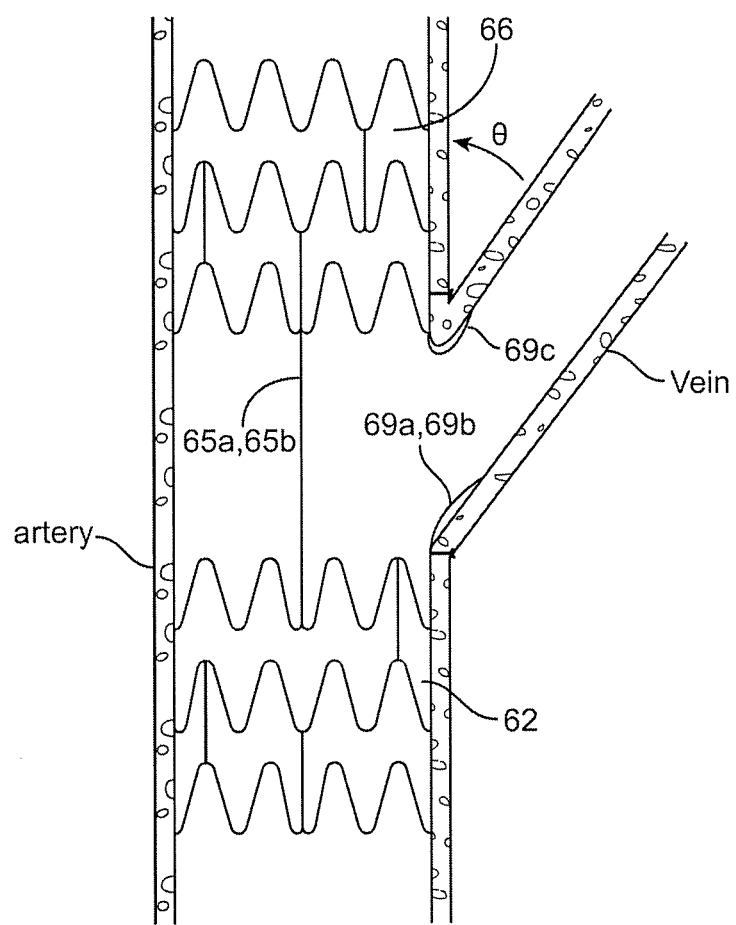
FIG. 3F shows a side-view of the stent or scaffold of FIG. 3E when implanted in the arterial portion of the AV fistula.

There are two straight connectors 65*a*, 65*b* separated by 180 degrees, which connect a proximal end 66*a* of the portion 66 to a proximal end 62*a* of the portion 62. Extending between the proximal ends 62*a*, 66*a* are petals 69 that are heat-set to deflect outward when the stent 60 is released from a constraining sheath. Referring to FIG. 3F there is shown a view of the stent 60 when implanted at the fistula. The petals 69*a*, 69*b* connected to downstream portion 62 are configured to fold outward and in a different direction (i.e., clockwise in FIG. 3F) from the petal 69*c* connected to upstream portion 66, which folds outward and counterclockwise in FIG. 3F. The final angles taken by the petals 69 are such as to support the connected vein at the take-off angle Θ. A petal 69 may be a U-shaped element as shown. The petal 69 may extend from a crown of a ring to a different crown of the same ring.

The petals 69 shown in FIG. 3E extend between and are connected to different U-crowns of the same ring.

Figure 3G:
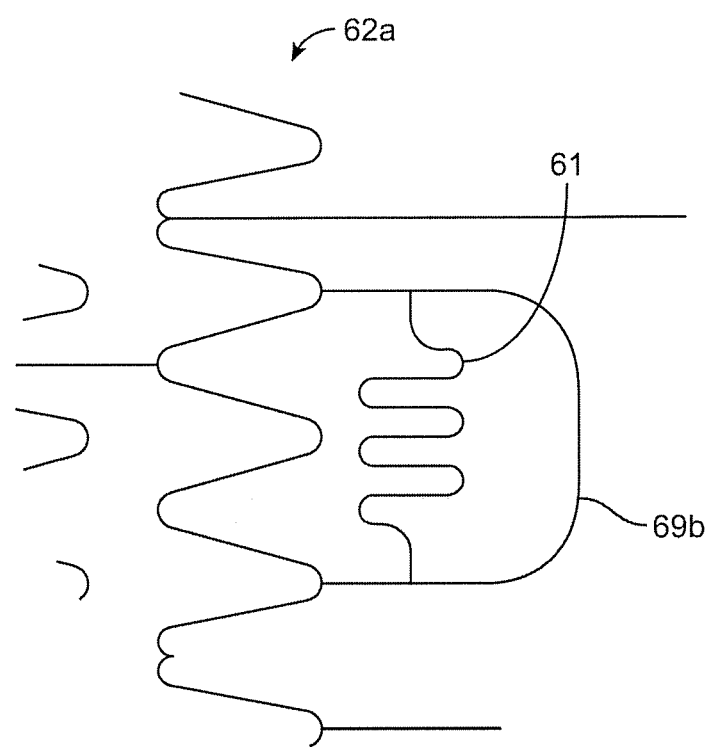
FIG. 3G is a portion of the scaffold of FIG. 3E showing a compressible wire structure within a space formed by a support petal.

As mentioned earlier, it is desirable to fill open spaces for a supporting structure to limit prolapse. With regard to a supporting structure an example of this structure is shown in FIG. 3G. There is an undulating structure 61 formed within the wire forming petal 69b. The structure 61, also of a wire, is capable of being compressed to accommodate the shape of the petal 69b when constrained within the sheath. The structure has a plurality of curves to give it a relatively low stiffness and the desired compressibility, and achieve the function of filling the space surrounded by the petal 69b.

Referring to FIG. 4A, there is shown a cross-sectional side view of the medical device 100 of FIG. 1A located at the distal end 4a of the delivery catheter 4. The catheter 4 is controlled from a proximal end 4b. The catheter 4 is preferably curved as shown such that its distal end turns through an angle of between about 60 to 90 degrees. The curvature may extend over the length of the sheaths 102, 106 that restrain the stent 10. For example, as measured between the proximal end 106b of the sheath 106 and distal tip 102a of sheath 102 the distal end 4a may turn through the angle of between about 60-90 degrees. This curvature facilitates placement of the tubular portion 12 in the artery and tongue 16 at the opening 2 when the catheter 4 enters the artery from the opening 2, as illustrated in FIGS. 1A-1F.

As briefly discussed earlier in connection with FIGS. 1A-1F, the medical device 100 includes a first sheath 102 located at the distal tip of the catheter 4 and configured for restraining the tubular portion 12 of the stent 10. A second sheath 106, located proximally of the sheath 102, restrains the tongue 16 of the stent 10. The first sheath 102 is pushed off the tubular portion 12 using a rod or pusher 107 operable from the catheter proximal end (not shown). The pusher 107 has a distal tip 107a connected to the sheath 102 at sheath end 102a, both of which are located distally of the stent 10. The rod 107 may also form a lumen for passage of the guidewire 5 through the catheter 4 distal end 4a (FIG. 1A). The second sheath 106 is pulled off the tongue 16 when the tongue is disposed at the opening 2. The sheath 106 may be pulled off from the catheter 4 proximal end by a rod, tether or tube 109 connected to the second sheath proximal end 106b.

The stent 10 is mounted on a member 104 portion of the catheter distal end 4a. The member 104 is tubular in shape and forms a lumen 104c for passage of the rod 107 therethrough. The rod 107 may pass from a catheter proximal end (not shown) to a distal end 104a of the member 104. Formed at the distal end is a first ledge, lip, flange or abutment 104a circumscribing the lumen formed by member 104. Proximal of the ledge 104a is a second ledge 104b that at least partially surrounds the member 104 lumen. The stent 10 is retained between the two ledges 104a, 104b, which restrain the stent 10 from movement relative to member 104 along the catheter longitudinal axis. The restraint of the stent 10 longitudinally may be an interference fit provided by the ledges 104b, 104a. As shown in FIG. 4A the tongue 16 is adjacent to, and distal of the ledge 104b and the tubular portion 12 is adjacent to, and proximal of the ledge 104a. The first sheath 102 surrounds and provides a radial restraint on the tubular portion 12. The second sheath 106 surrounds and provides a radial restraint on the tongue 16.

Referring again to FIGS. 1A through 1D and FIGS. 2A, 2B and 4A, the curved catheter 4 including the medical device 100 is delivered along the guide wire 5 to the site of the anastomosis in the following manner. The catheter portion containing the sheath 102 (and tubular portion 12) is positioned so that the proximal end of tubular portion 12 is located immediately upstream of the opening 2 and so that the connector portion 15 will deflect the flange 16 outwardly to take the supporting position as shown in FIG. 1C when the sheath 106 is removed.

The sheath 102 is then pushed off the tubular 102 portion by pushing the rod 107 towards the catheter distal end 4a. Referring to FIG. 1C, when the sheath 102 is pushed off, it occupies the area 3a upstream of the tubular portion 12. After the sheath 102 has deployed the sheath 102 may be pulled back through the bore of the tubular portion 12. Next, the sheath 106 is removed from the flange 106.

By utilizing a catheter curved through an angle of about 60-90 degrees, a portion or substantially the entire flange 16 may be disposed outside of the opening 2 before the sheath 106 is removed and after the sheath 102 is removed. This configuration minimizes the chance of having the tongue 16 end catch on the walls of the opening 2 when tongue 16 is deflected outwardly by connector 15 after the sheath 106 is pulled off the tongue 16.

In alternative embodiments the member 4 may include a balloon to assist with expanding the stent 10 to take the position shown in FIG. 1C. The balloon would occupy the space on member 104 where the tubular portion 12 is mounted.

Figure 4B:
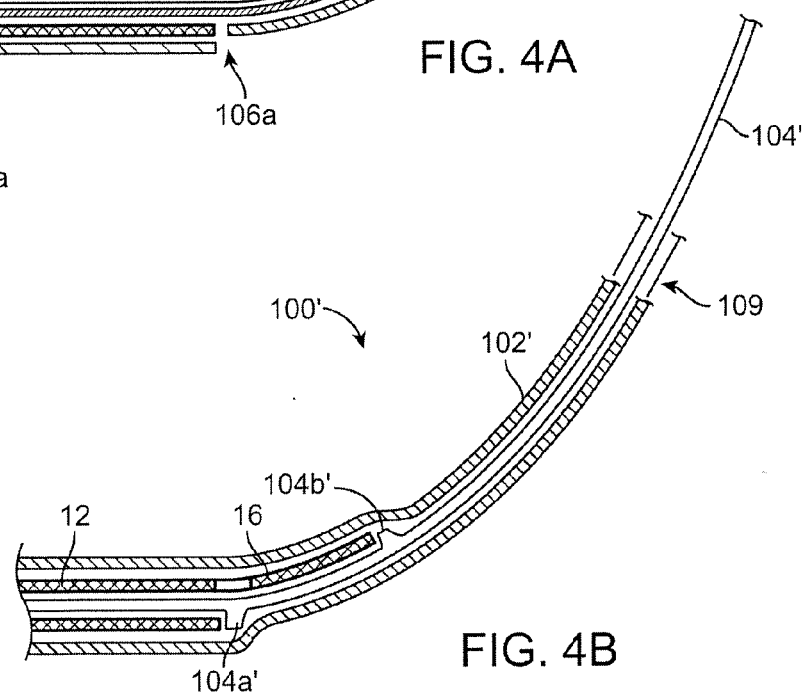
FIG. 4B is a partial view of a first alternative embodiment of a distal end of the catheter of FIG. 4A. According to this embodiment the stent or scaffold is self-expanding.

Referring to FIG. 4B there is shown a partial cross-sectional view of an alternative embodiment of a medical device 100' located at the catheter 4 distal end. This embodiment, in contrast to the medical device 100 shown in FIG. 4A, uses a single sheath 102' to restrain both the tubular portion 12 and tongue 16. The sheath 102' is pulled off by a tether 109 or tubular member 109, as was the case with sheath 106. Since there is no push-off sheath 102 for medical device 100' the push rod 107 is not needed. The member 104' may be configured the same as described for member 104, except there is no lumen needed for the rod 107, and the member 104' may only provide a lumen for passage of the guidewire 5 through the distal tip. Additionally, there is an additional ledge 104a', distal of a ledge 104b' and proximal of the ledge 104a (not shown). This intermediate ledge 104a' helps tubular portion 12 deploy when sheath 102' is pulled off without causing the stent 10 to shift towards the proximal end.

The stents 10, 20, 30, 40, 50 or 60 may be configured as self-expanding stents made from a super elastic metal alloy, such as nitinol. In alternative embodiments there are scaffolds having a tubular portion and tongue as described above where the material used is a self-expanding biodegradable, non-degrading or bioresorbable polymer, or biodegradable metal or combination thereof.

In other embodiments the tubular portions 12, 22, 32, 42, 52, 62 and 66 are balloon-expandable stents or scaffolds 10, 20, 30, 40, 50 or 60, respectively, as described in connection with FIGS. 1A-1F, 2A, 2B and FIGS. 3A-3F. The stents or scaffolds are configured into a crimped, stowed configuration then in-elastically configured from the crimped configuration to a deployed configuration by balloon inflation. In these embodiments the stents or scaffolds are crimped onto the balloon, then deployed by balloon inflation to assume an expanded state. In a particular embodiment the tubular portion may be made to have an appreciable level of crush-recovery. According to these embodiments the scaffold for the tubular portion of the stent 10 may have the properties of a crush-recoverable and balloon expanded scaffold as described in US 2011/0190871 including Tables 2, 3, FIGS. 2, 4 and paragraphs [0200], [0204] and [00131]-[00144].

Figure 4C:
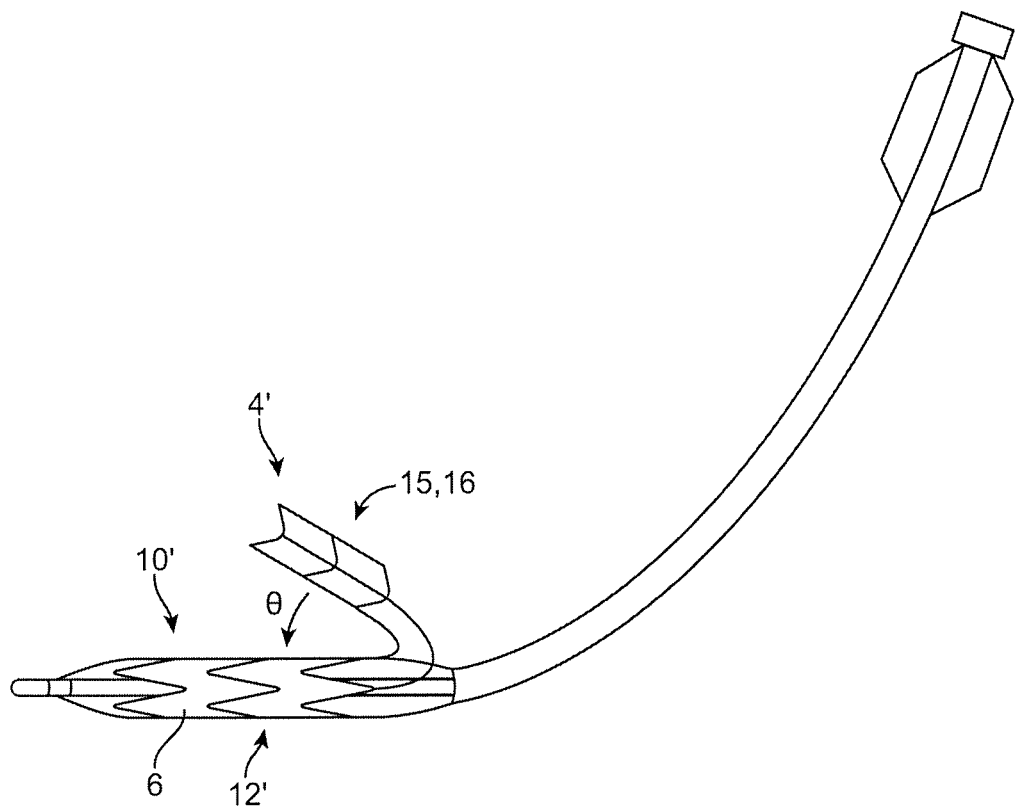
FIG. 4C is a side-cross sectional view of a second alternative embodiment of a distal portion of the catheter of FIGS. 1A-1F used to deliver the stent or scaffold of FIGS. 2A-2B. According to this embodiment the stent or scaffold is balloon expandable.

Referring to FIG. 4C, for a balloon expandable stent or scaffold the connector 15 and tongue 16 may be pre-configured in the deployed state before entry into the opening 2 of the artery. Assembly of this implant may include the following steps: cut the tubular portion 12' from a tube, attach the connector 15' and tongue 16' (or cut 15' and 16' from the same tube), crimp the tubular portion 12' to the balloon 6 of the catheter 4', then shape the connector 15' and tongue 16' to form the take-off angle Θ.

Figure 5A:
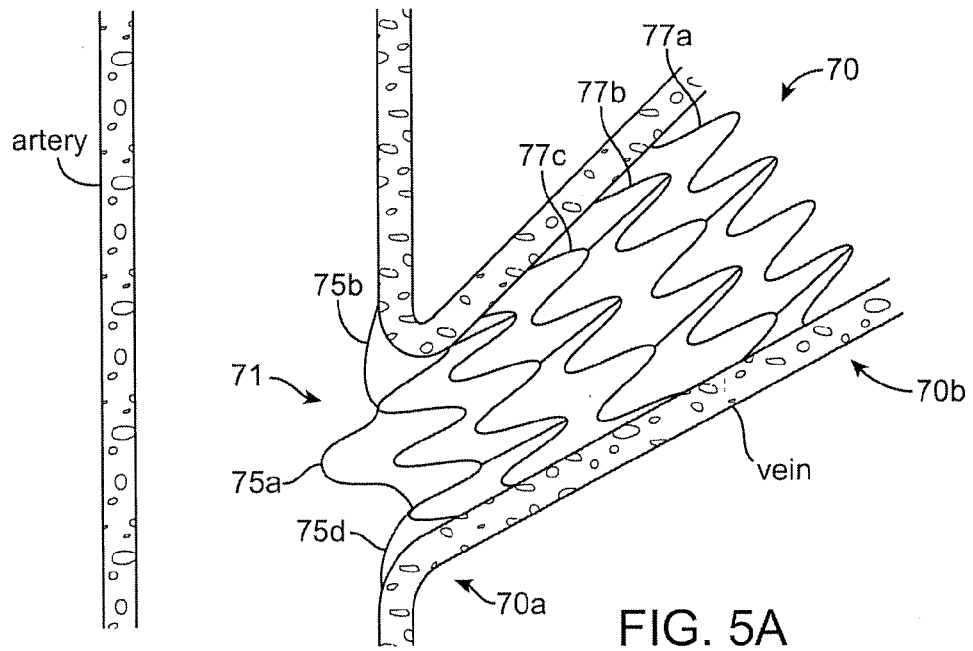
FIG. 5A shows a side view of a venous stent or scaffold supporting an AV fistula in accordance with a second aspect of the disclosure.
Figure 5B:
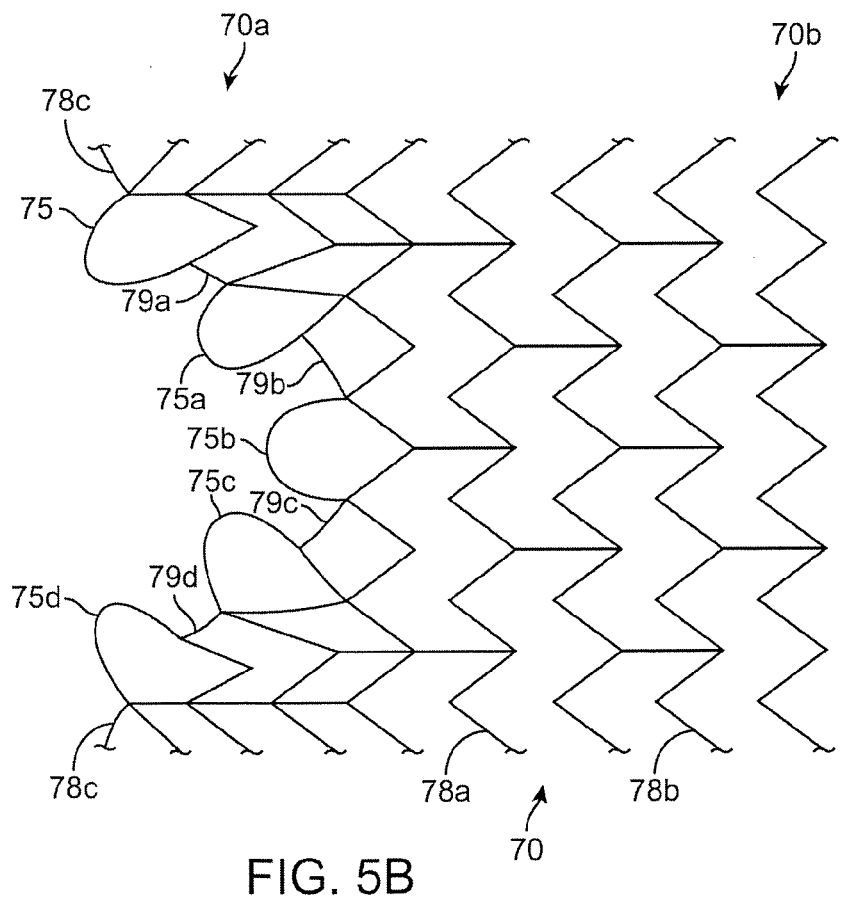
FIG. 5B is a 2D flattened view of the stent or scaffold of FIG. 5A.

With reference to FIGS. 5A-5B, according to another aspect of the disclosure there is a frustoconical intraluminal stent (or scaffold) 70 placed in the venous portion of an AV fistula. The frustoconical stent 70 has a larger diameter at its end 70b that is placed furthest from fistula, as compared with the end 70a closest the fistula upon implantation. Additionally, there is preferably a bevel and petals at distal end 70a which help maintain the take-off angle Θ. The pattern shown in FIG. 5B is that of a cylindrical body, but can be formed in such a way as to make it a frustoconical body. For example, in the case of a self-expanding stent or scaffold the body can be set to form a frustum when a restraining sheath (not shown) is removed.

Or, if balloon expandable the tubular body in FIG. 5B could achieve frustoconical shape by using a conical balloon to expand it. Additionally, the ring geometry may vary in proportion to the amount of taper desired. For example, referring to FIGS. 5A-5B the number of crests would increase from end 70a towards end 70b, or the length of bar arms 78a, 78b that form crests. With longer bar arms the rings closer to end 70b can be expanded to a larger diameter that rings closer end 70a. Thus, for example, for a first taper ratio of T1 the length of the bar arms for the end ring at 70b would be T1 times longer than the bar arm at proximal end 70a. FIG. 5A shows the implanted frustoconical stent 70 at the venous portion of the fistula with a portion extending into the artery.

The stent 70 may be configured at the time of implantation to have no taper and develop a tapered shape about two weeks after implantation. In this embodiment the frustoconical stent 70 constrained to have a cylindrical shape may include biodegradable structure that causes the stent 70 to develop the tapered shape at about the same time the vein is expected to mature into a larger diameter due to increased blood flow from the connected artery. As such the stent 70 changes shape to accommodate or encourage an enlarging vein. The restraining structure may be applied to a self-expanding body that when unrestrained forms the frustoconical stent 70. The restraining material can be a fiber, band or filament made from a biodegradable polymer, a rapidly degrading biodegradable metal such as magnesium; or a biocompatible protein such as gelatin or collagen.

The fiber, band or filament may be wrapped about the stent body near the proximal end 70b (e.g., wrapped in a helical or crisscross fashion and looped through openings between struts/links of the stent) to restrain the proximal end 70b from expanding out to form a larger diameter than the distal end (the proximal end 70b may have a target or set diameter that is about 2, 3, 4, or between 3-6 times larger than the distal end 70a diameter after the restraining material has degraded sufficiently as to not be capable of restraining the stent 70 from radially expanding to the pre-set tapered shape, e.g., the heat set tapered shape in the case of a nitinol self-expanding stent 70. The filaments are wrapped such that they become taught when the stent 70 expands out to the final diameter of the distal end 70a). After the restraining filaments have degraded sufficiently and released the stent 70 expands outwardly further to form a frustum. This outward expansion may facilitate growth of the fistula if it is not so forceful as to cause injury. Self-expanding stents generate an outward radial force until they reach their set or target diameter.

FIG. 5A shows a side-view of the stent 70 implanted at the fistula and FIG. 5B shows a flattened view of the stent 70. The flattened view of FIG. 5B shows a pattern for a cylindrical body, whereas FIG. 5A shows a frustoconical body adopting a similar pattern as shown in FIG. 5B.

The stent 70 includes at the distal end 70a petals, a tongue, or flange 71 that is intended to extend at least partially into the lumen of the artery for purposes of maintaining the take-off angle Θ. To this end, the distal end 70a may be beveled and include a tongue, flange, or petals extending into the lumen of the artery and being flush with artery walls. The stent 70 may be made of a self-expanding alloy such as elgiloy, work hardened stainless steel, or nitinol. Self-expanding bioresorbable materials are possible as well. These embodiments may include hardened iron and bioresorbable polymers.

Referring again to FIG. 5B there is shown a 2D depiction of the stent 70 having the bevel at the edge of end 70a. When the 2-D structure depicted in FIG. 5B is rolled up, it will have a beveled edge. The point near label 75b will be the shortest length of the stent, and the other side (180 degrees apart) will be the longest length.

The bevel is preferably half a sinusoid in shape, extending between the strut portions 78c and 78c' and taking the half-sinusoid shape by following along the bevel supporting links 79d, 79c, 79b, and 79a. Inter-disposed among the links 79d, 79c, 79b, and 79a are petals 75, including petals 75a, 75b, 75c and 75d. For a nitinol stent the petals 75 are set to deflect outwardly as shown in FIG. 5A.

The bevel is placed adjacent the carina of the fistula in FIG. 5A when the device is implanted. With respect to FIG. 5A the bevel preferably extends over the 180 degrees circumference of the end 70a. The other 180 degrees of the circumference is straight or without the bevel, i.e., like the end 70b in FIG. 5B. The bevel is desired in this location to minimize interference with blood flow from the artery to the vein. Referring to FIG. 5B, the 2D representation of the stent (or scaffold) shows about 180 degrees of the circumference extent of the body. The remaining 180 circumferential extent (over the length of the body 70), which is not shown in FIG. 5B, may have the same repeating pattern of the rings 78a, 78b and connecting links discussed herein for the self-expanding stent or balloon expandable scaffold or stent.

Delivery of the stent 70 to the fistula may be accomplished via at least two methods. In the first method, the stent 70 is mounted onto a catheter with a restraining sheath, but the stent 70 is not restrained by filaments to take the form of a cylindrical body; that is, upon removal from the constraining sheath the stent 70 begins to take on a frustoconical shape. The proximal end 70b therefore may become larger than the arterial opening 2 of the anastomosis and vein luminal diameter before the vein is attached to the artery. The method may thus proceed so that the stent 70 is not fully deployed until after the fistula is formed, so as to avoid injuring the vein.

Figure 6A:
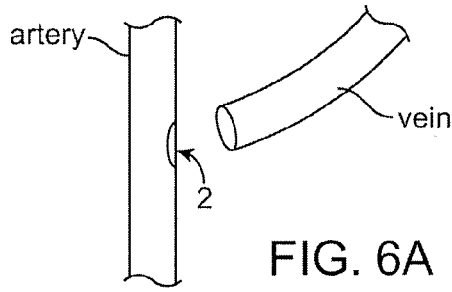
FIGS. 6A-6H depict steps associated with a procedure for forming an AV fistula using the stent or scaffold of FIGS. 5A and 5B.
Figure 6B:
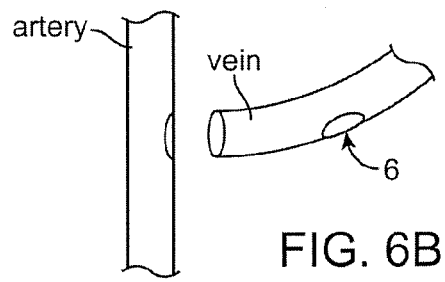
Figure 6C:
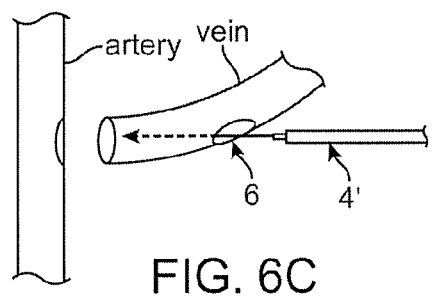
Figure 6D:
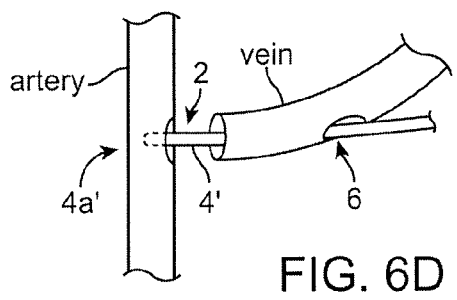
Figure 6E:
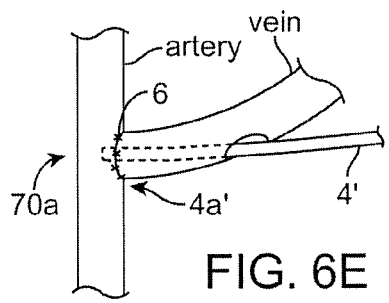
Figure 6F:
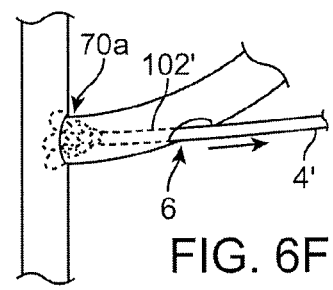
Figure 6G:
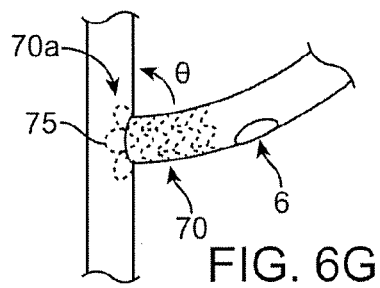
Figure 6H:
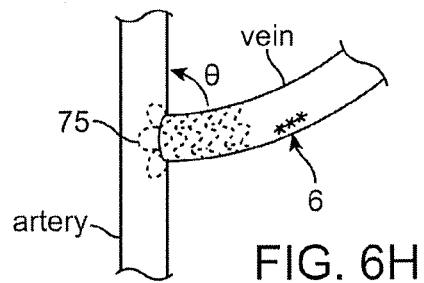

Examples of steps practicing the first method of implanting the stent 70 are shown in the FIGS. 6A-6H. The opening 2 is made in the artery. An opening 6 is also made in the vein for passage of a catheter 4' with stent 70 mounted thereon through the opening 6 and towards the opening 2. The catheter 4' (with or without guide wire 5) is then passed through the openings 2 and 6 such that the distal end 4a'/70a' is disposed within the artery at the opening 2. These steps are shown in FIGS. 6A-6D. The vein is attached to the artery while the catheter distal end 4a' remains at the opening 2 and the catheter 4' extends through the opening 6. After the fistula is formed, the sheath 102' is removed from the stent 70 by pulling the sheath 102' off the stent 70 (FIGS. 6E-6F). After the sheath 102' is removed and the catheter 4' withdrawn, the stent 70 expands to have the beveled edge/distal end 70a at the carina at the anastomosis and petals 75 flush with artery walls, which stent 70 structure holds the vein at the desired take-off angle $\Theta$. The vein opening 6 is sutured. These steps are shown in FIGS. 6F-6H.

In a second method for delivery of the stent 70 restraining filaments are wrapped around the stent 70 to restrain the stent 70 from forming a frustum when released from the sheath 102'. Instead, the stent 70 proximal end 70b when removed from the sheath 102' expands no more than about the diameter of the stent 70 at the distal end 70a. In contrast to the first method the stent 70 therefore may be placed at the artery opening 2 and sheath 102' withdrawn before the fistula is made. Examples of steps practicing the second method of implanting the stent 70 are shown in the FIGS. 7A-7F.

The opening 2 in the artery is formed and the catheter 4' placed without first passing the catheter 4' through the vein. The sheath 102' is withdrawn, thereby allowing the stent 70 to expand to have the beveled edge/distal end 70a at the opening 2 with the petals 75 flush with artery walls, which stent 70 structure holds the vein at the desired take-off angle $\Theta$. The catheter 4' is then removed and the vein is placed over the stent 70. Due to the presence of the constraining filaments 78 the proximal end 70b is restrained to have no more than the expanded diameter as the distal end 70a. This allows the vein to be easily slipped over the stent 70, which functions as a guide for the surgeon attaching the vein to the artery. These steps are shown in FIGS. 7A-7D.

Figure 7A:
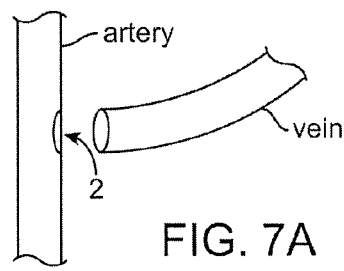
FIGS. 7A-7F depict steps associated with a procedure for forming an AV fistula using an alternative embodiment of the stent or scaffold of FIGS. 5A and 5B.
Figure 7B:
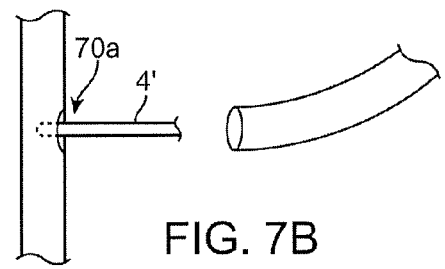
Figure 7C:
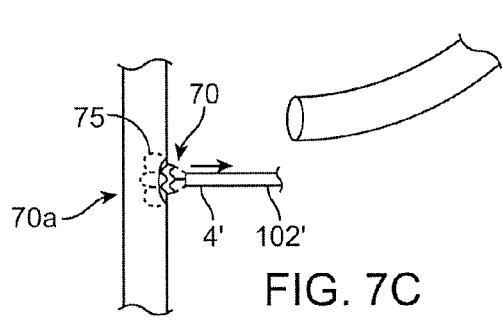
Figure 7D:
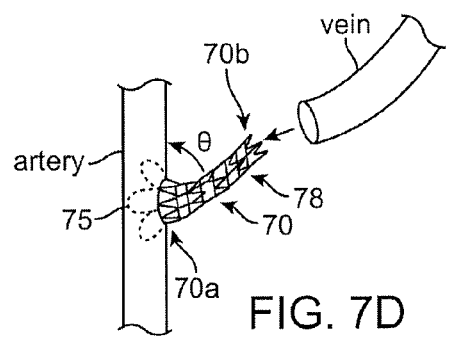
Figure 7E:
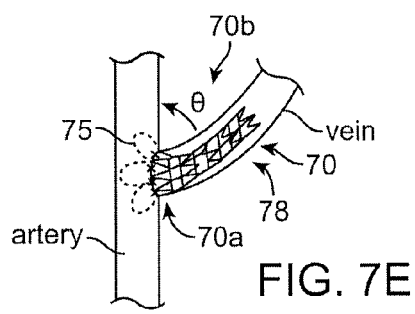
Figure 7F:
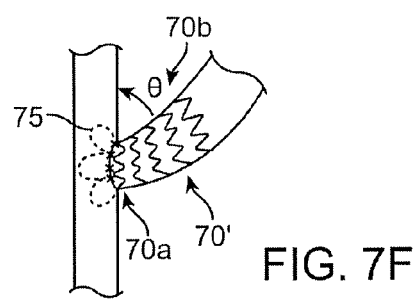

Referring to FIG. 7E, after the fistula is formed the stent 70 structure holds the vein at the take-off angle $\Theta$ (as before) and the filaments 78 restrain the stent proximal end 70b. Referring to FIG. 7F, after an about 10 minute to 4 week period, or more, the filaments 78 degrade sufficiently as to no longer resist the radial outward force of the stent 70. By this point the vein has increased in diameter and the frustum pre-set shape for the stent 70 conforms to the maturing vein lumen. At end 70b, the outward force exerted by the stent may assist in dilation and maturation of the AV fistula In accordance with another aspect of invention there is a balloon catheter having a balloon that when inflated forms an angled shape for purposes of assisting or acting as a guide for formation of an AV fistula having the desired take-off angle $\Theta$. The illustrated embodiments include two balloon types—a single lobe balloon 200 (FIGS. 9 and 8A-8J) and double lobe balloon 210 (FIGS. 10A-10C, 11A, and 11B).

Figure 9:
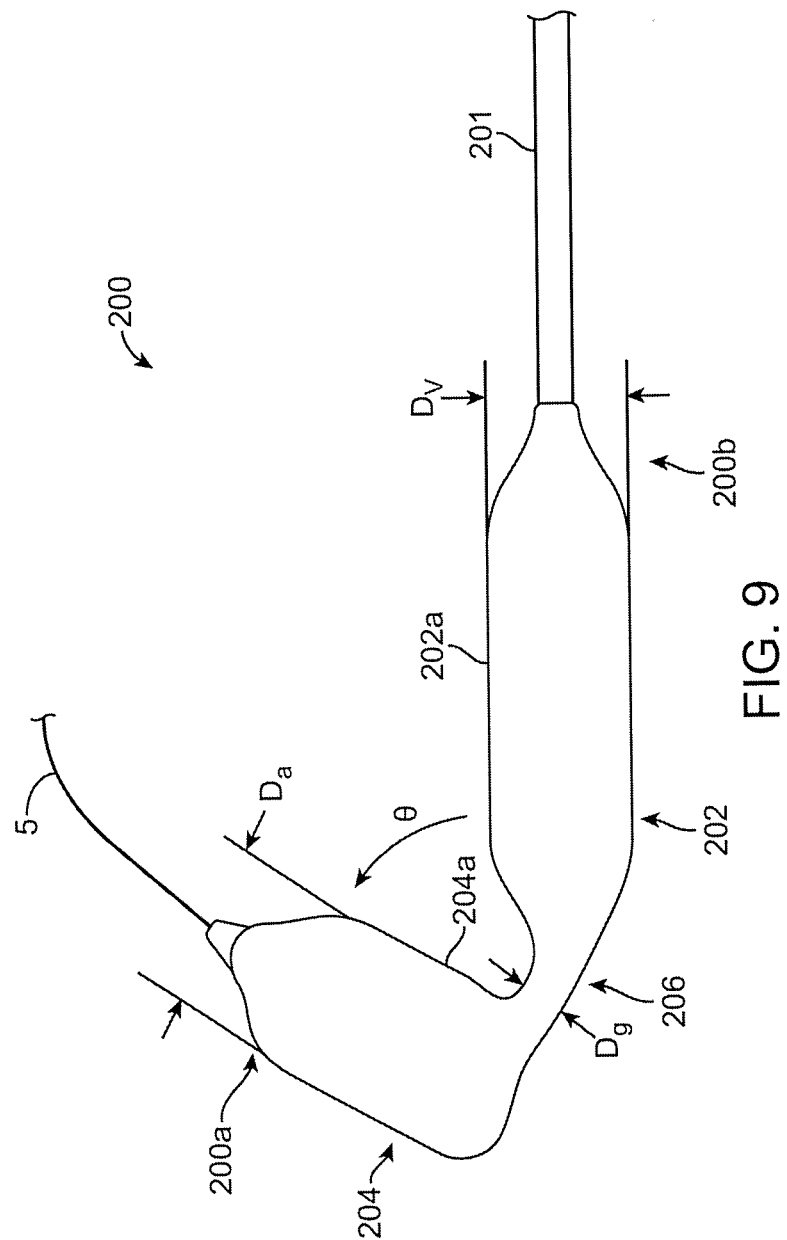
FIG. 9 shows an inflated state for the balloon of the catheter used in the steps of FIGS. 8A-8J.

Referring first to FIG. 9, there is shown a distal portion of a catheter having an inflated, angled balloon 200. At the distal end 200a there is an exit for the guide wire 5 and the catheter provides an inflation lumen 201 proximally of the balloon 200. The balloon 200 has a proximal portion 202 configured to support the venous portion of the fistula, a distal portion 204 configured to support the arterial portion of the fistula; and an intermediate portion 206 positioned at the location where the artery and vein are sutured together at the opening 2. The balloon 200 is intended to function essentially as a guide for forming the fistula with the desired angle $\Theta$. The balloon may be drug-coated with a drug such as paclitaxel, or a taxane, in order to provide drug therapy. Prevention of anastomotic hyperplasia that could lead to restenosis would be the goal. The angled balloon system including the catheter, balloon 200 and guidewire 5 may have the following features:

The guidewire 5 may have a preformed angle $\Theta$ to introduce the balloon 200. A guidewire made of nitinol is one approach.

The balloon 200 is preformed to have the angle $\Theta$ when inflated. Both noncompliant and semi-compliant balloons can be made to take the shape depicted in FIG. 9 when the balloon 200 is inflated.

Between the distal arterial portion 204 of the balloon 200 and the proximal venous portion 202 there is the intermediate or waist portion 206. The waist 206 is narrower than the portions 202, 204 (i.e., in FIG. 9 the diameter Dg of the waist 206 is less than Da and Dv of the arterial portion 204 and venous portion 202, respectively; moreover, Da>Dv>Dg) and is designed to allow the anastomosis to be made more easily without interference of balloon material situated against the lumen where the anastomosis will be made. By having a gap between the balloon 200 and the vessel wall at the anastomosis, the surgeon can avoid puncturing the balloon 200 when joining the artery and vein.

As no lesion or stenosis is being dilated, the balloon 200 does not have to be non-compliant. It can be semi-compliant, or even compliant.

Again referring to FIG. 9, the balloon surfaces that provide the stated guide for the angle $\Theta$ are surface 204a of the arterial portion 204 and surface 202a of the venous portion 204. The waist portion 206 extends through the opening 2 of the artery and has an outer diameter Dg that provides sufficient clearance so as to not interfere with suturing the vein to the artery.

Figure 8A:
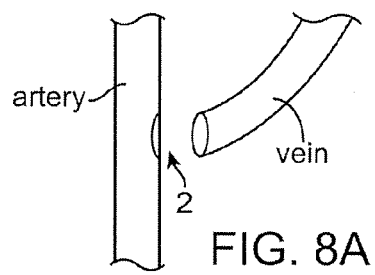
FIGS. 8A-8J depict steps associated with a procedure for forming an AV fistula using a catheter having an angled balloon in accordance with a third aspect of the disclosure.
Figure 8B:
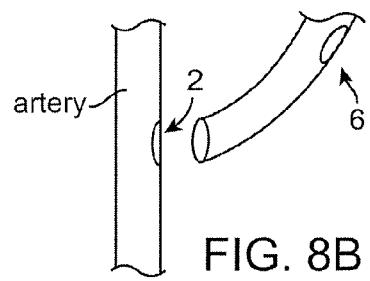
Figure 8C:
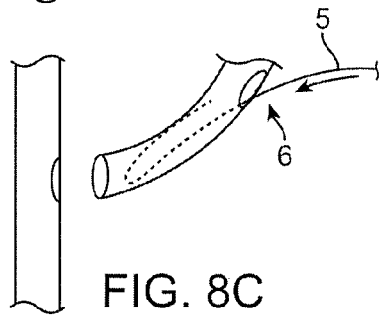
Figure 8D:
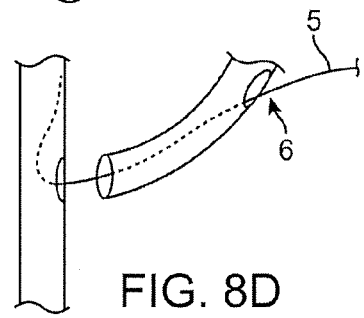
Figure 8E:
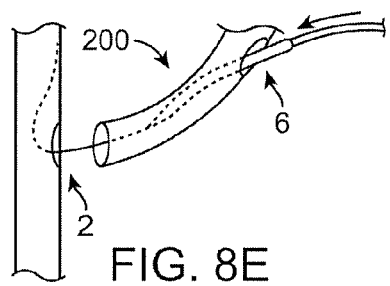
Figure 8F:
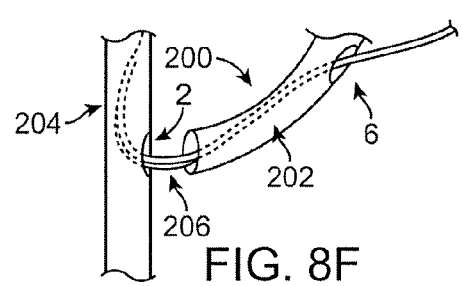
Figure 8G:
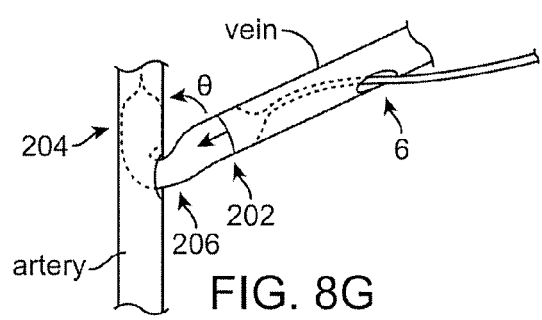
Figure 8H:
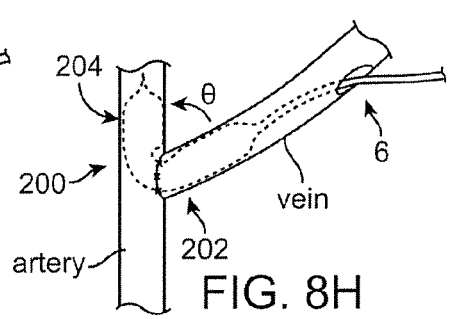
Figure 8I:
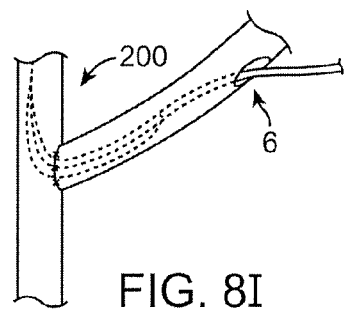
Figure 8J:
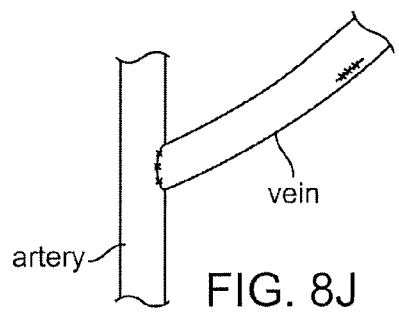

Referring now to FIGS. 8A through 8J, as before the opening 2 is formed in the artery and the opening 6 is formed in the vein. The curved guidewire 5 is then passed through opening 6 then opening 2. The catheter with balloon 200 is then passed over the guidewire 5 to position the arterial portion 204 within the lumen of the artery and the intermediate or waist portion 206 disposed at the opening 2 where the anastomosis will be made (FIG. 8F). The balloon 200 is then inflated and forms the angle $\Theta$. Saline or contrast may be used to inflate the balloon 200. The vein is passed over the portion 202 which guides the vein to the opening 2 with the desired orientation, so that when sutured the vein will extend from the anastomosis at the take-off angle $\Theta$ (FIG. 8G). In one embodiment, the cut edge of the vein is advanced over the inflated portion 202 and the anastomosis formed at the targeted angle. In another embodiment, the cut edge of the vein is approximated first and then the balloon 200 inflated. The anastomosis would be formed by suturing, thermal bonding, or adhesive bonding. The balloon 200 is then deflated and removed from the vasculature (FIGS. 8H-8J). To maintain the angle $\Theta$ further steps may include delivery of the stent 70 through the vein from a more proximal location or distal location via an opening 6 (FIG. 6F), or placement of an extravascular wrap as described in connection with FIGS. 3, 4 and 5 of the '984 application.

According to another embodiment two guide wires may be used with the balloon 200. Both guidewires are introduced into the proximal vein portal, slit or opening 6, passed through the vein, and into the artery. One guidewire is passed upstream through the artery and the other passed downstream through the artery. The upstream artery is pre-shaped to have the angle $\Theta$ and the downstream artery is pre-shaped to have an angle of (180°−$\Theta$). After placement of these two wires, the balloon 200 is passed over only the downstream guidewire. The downstream guidewire is external of the balloon 200 and pressed against the arterial/venous wall opposite the carina when the balloon 200 is inflated and when the fistula is being made. The two guide wires may be desired to both guide the balloon and control the balloon inflated position with respect to the desired angle Θ and/or to assist with forming the anastomosis at the desired angle.

According to another aspect of the disclosure there is a "two-headed," "Y" shaped, or double lobed balloon. One lobe would be in the vein, one lobe in the artery upstream of the opening 2, and one lobe in the artery downstream of the opening 2. This balloon (FIG. 11A) would include two guidewire lumens, one for each arterial balloon lobe. It would be advanced over both guidewires 215a, 215b but the two lobes would part as they passed into the artery, each lobe riding over its own guidewire. This scenario would define the geometry of the vein relative to the proximal and distal artery in a very complete manner. All balloon lobes could be on the same inflation lumen. However, it is possible that each lobe could be on its own inflation lumen although a catheter with two guidewire lumens and three separate inflation lumens is intricate. With the double, "two-headed" or "Y" shaped balloon, after the balloon is inflated the vein would be slid into place and the anastomosis made. Afterwards, the system is deflated and all guidewires and the balloon catheter withdrawn through the vein opening 6.

Figure 11A:
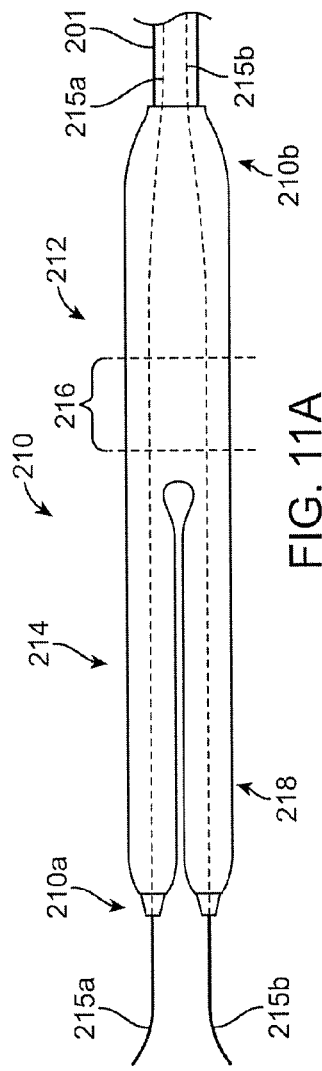
FIGS. 11A-11B shows deflated and inflated states, respectively, of the catheter having the angled balloon used in the steps of FIGS. 10A-10C.
Figure 11B:
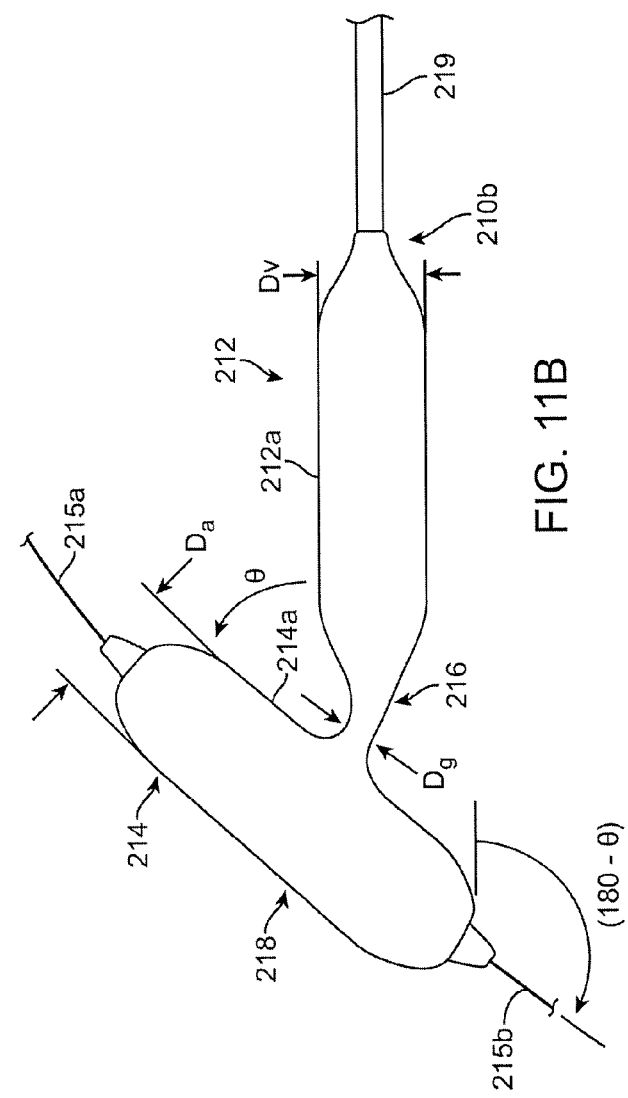
Figure 12:
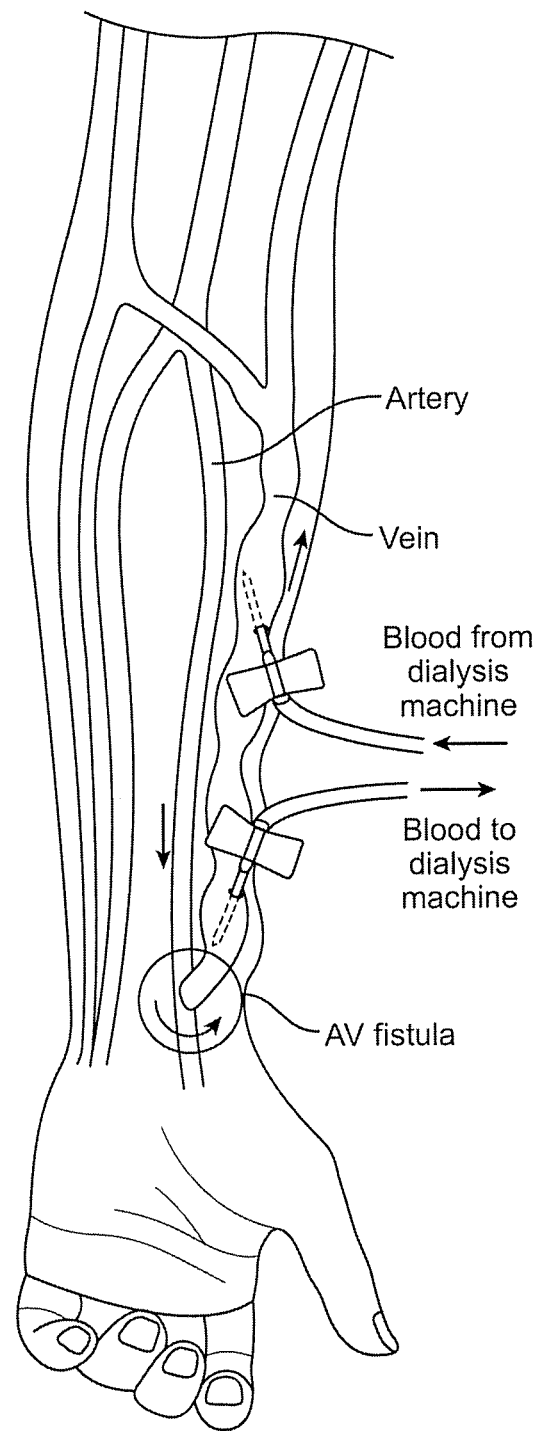
FIG. 12 is a side-view of an arm of a patient receiving dialysis. A fistula is shown.

Referring to FIGS. 11A and 11B there is shown deflated and inflated states, respectively, for one example of the double lobed balloon 210. The double lobe refers to distal balloon portions 214, 218 that are guided along separate guidewires 215a and 215b to arterial locations immediately downstream and upstream of the arterial opening 2 where the anastomosis is made. The waist portion 216 has the same attributes as waist portion 206 and demarcates the distal double-lobe portions 214, 218 from the proximal portion 212. The double lobes 214, 218 are folded over one another and travel together over the guidewires 215a, 215b. Each have their own guidewire lumen from the waist portion 216 to the distal end 210a. The proximal end 210b of the balloon 210 provides passage for the two guidewires 215a, 215b and may share the same lumen proximal of the waist 216. The upstream guidewire 215a may be pre-shaped to form the angle Θ and the downstream guide wire 215b may be pre-shaped to form the angle 180°-Θ degrees. When inflated the lobes 214, 218 extend along the artery and across the opening 2 and form the respective angles Θ and (180°-Θ) with respect to the longitudinal axis of portion 212 and catheter portion 219, as shown in FIG. 11B.

Figure 10A:
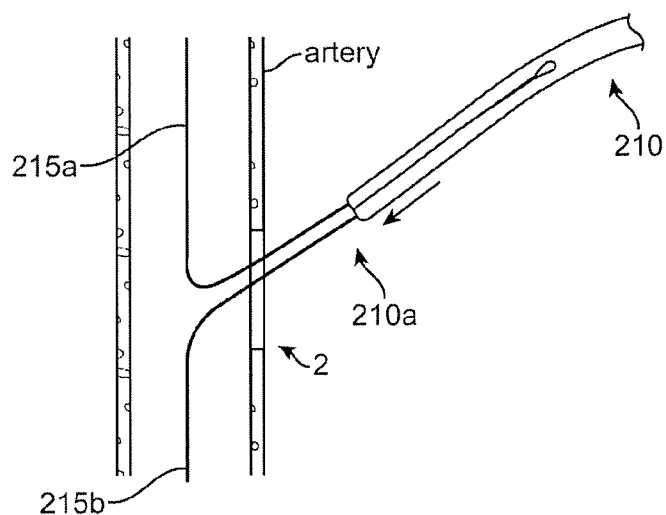
FIGS. 10A-10c depict steps associated with a procedure for forming an AV fistula using a catheter having an alternative embodiment of the angled balloon of FIG. 9.
Figures 10B, 10C:
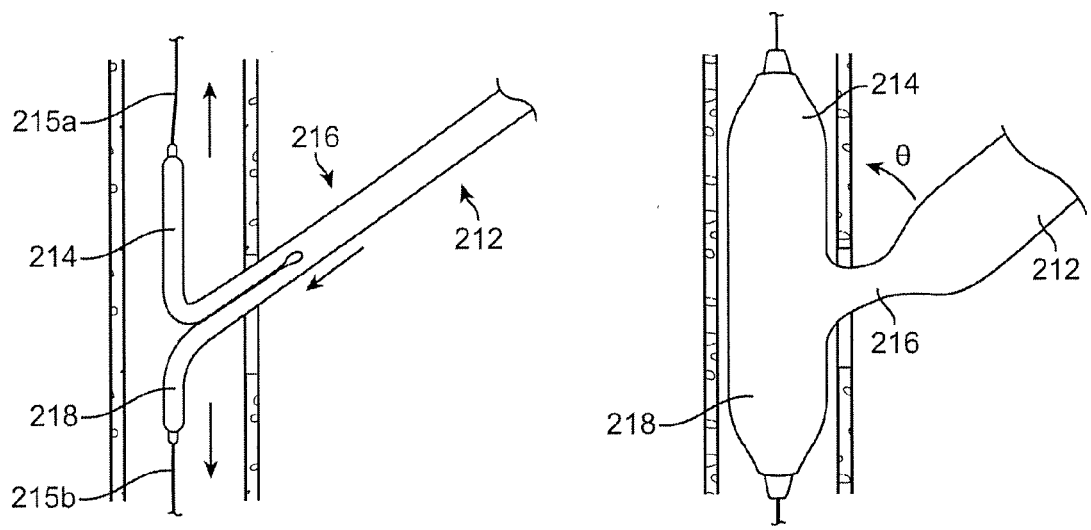

Referring to FIGS. 10A-10C, there is shown aspects of a method for placing the balloon 210 when the fistula is formed. After the opening 2 is formed (as before), the guidewires 215a, 215b are placed at their respective upstream and downstream locations as shown. The balloon 210 is passed over the guidewires 215a, 215b. After entry through the opening 2 the lobes separate as they travel along their respective guidewires. The waist 216 is located at the opening 2 as before. The balloon 210 is inflated whereupon the vein is moved in place and sutured to the artery.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. An intraluminal medical device, comprising:
   a stent or scaffold, including
   a tubular portion,
   a tongue having a proximal end arc length and a distal end arc length, each spanning an angle of 270, 180 or 90 degrees, or about 90-180 degrees, wherein the tongue has a taper of ratio of between 1:1.5 to 1:3 such that the distal end arc length is lamer than the proximal end arc length; and
   a connector connecting the tongue to the tubular portion;
   wherein the connector is pre-shaped to cause the tongue to form an angle (Θ) of about 30 or between about 15 to 45 degrees with respect to a bore axis of the tubular portion.

2. The medical device of claim 1, wherein the tubular portion is a radially expandable body having a plurality of rings interconnected by struts.

3. The medical device of claim 1, wherein the connector comprises a plurality of link elements.

4. The medical device of claim 1, wherein the connector includes a first plurality of links interconnected by a second plurality of links through a transitional structure.

5. The medical device of claim 1, wherein the tongue is a paddle.

6. The medical device of claim 1, wherein the connector includes a central, straight connector and two S-shaped connectors surrounding the straight connector.

7. A catheter comprising the medical device of claim 1 retained within a sheath at a distal end of the catheter.

8. The catheter of claim 7, wherein a first sheath constrains the tubular portion and a second sheath constrains the tongue.

9. The catheter of claim 7, wherein the tubular portion and tongue are retained between a proximal ledge and a distal ledge.

10. A medical device, comprising
    a catheter having a distal end and a proximal end, wherein the distal end is made with a curve such that the distal end curves through an angle of 60 to 90 degrees with respect to the proximal end; and
    the stent or scaffold of claim 1 mounted on the catheter.

11. The medical device of claim 10, further comprising
    a first sheath disposed over the tubular portion,
    a second sheath disposed over the tongue,
    a pusher connected to the first sheath, and
    a rod, tether or tube connected to the second sheath,
    wherein the first sheath and the second sheath are separately removable from the tubular portion and the tongue, respectively, using the pusher and tether, rod or tube.

12. The medical device of claim 11, wherein the pusher has a distal tip connected to the first sheath.

13. The medical device of claim 11, wherein the catheter further comprises a member having a lumen for passage of the pusher, the member having a first and second ledge, the first ledge circumscribing a bore axis for the lumen and the second ledge at least partially surrounding the bore axis, wherein the stent or scaffold is disposed between the first and second ledge.

14. The medical device of claim 10, wherein the tubular portion and tongue are self-expanding.

* * * * *